US012558347B2

(12) United States Patent
Patel et al.

(10) Patent No.: US 12,558,347 B2
(45) Date of Patent: Feb. 24, 2026

(54) CEVIMELINE LIQUID FORMULATIONS

(71) Applicant: Cosette Pharmaceuticals, Inc., Bridgewater, NJ (US)

(72) Inventors: Ravi Patel, East Windsor, NJ (US); Apurva Saraf, Princeton, NJ (US)

(73) Assignee: Cosette Pharmaceuticals, Inc., Bridgewater, NJ (US)

( * ) Notice: Subject to any disclaimer, the term of this patent is extended or adjusted under 35 U.S.C. 154(b) by 0 days.

(21) Appl. No.: 19/213,047

(22) Filed: May 20, 2025

(65) Prior Publication Data

US 2026/0034108 A1 Feb. 5, 2026

Related U.S. Application Data

(60) Provisional application No. 63/677,165, filed on Jul. 30, 2024.

(51) Int. Cl.

| | |
|---|---|
| ***A61K 31/439*** | (2006.01) |
| ***A61K 47/02*** | (2006.01) |
| ***A61K 47/10*** | (2017.01) |
| ***A61K 47/14*** | (2017.01) |
| ***A61K 47/18*** | (2017.01) |
| ***A61K 47/38*** | (2006.01) |

(52) U.S. Cl.

CPC ............ *A61K 31/439* (2013.01); *A61K 47/02* (2013.01); *A61K 47/10* (2013.01); *A61K 47/14* (2013.01); *A61K 47/183* (2013.01); *A61K 47/38* (2013.01)

(58) Field of Classification Search

None

See application file for complete search history.

(56) References Cited

U.S. PATENT DOCUMENTS

2019/0060462 A1* 2/2019 Tengler ................ A61K 9/4866

FOREIGN PATENT DOCUMENTS

MX 351321 B * 9/2017 ......... A61K 31/4178

OTHER PUBLICATIONS

Machine translation of MX351321B (Year: 2017).*

Villiers, "Antioxidants" In: Thompson, "A Practical Guide to Contemporary Pharmacy Practice" Wolters Kluwer Health/Lippincott Williams & Wilkins, 2009, 3rd edition, pp. 216-223 (Year: 2009).*

* cited by examiner

*Primary Examiner* — Adam C Milligan
*Assistant Examiner* — Jed A Kucharczk
(74) *Attorney, Agent, or Firm* — Mark A. Mazza; Lisa E. Geary; Eckert Seamans Cherin & Mellott LLC

(57) ABSTRACT

Liquid formulations including cevimeline hydrochloride and a combination of at least one sweetener and at least one flavoring agent to mask the bitter taste of the cevimeline hydrochloride when formulated for oral administration. A taste masking composition that masks the bitter taste of cevimeline hydrochloride when formulated for oral administration, wherein the taste masking composition includes two or more sweeteners and two or more flavoring agents. Liquid formulations including cevimeline hydrochloride and the taste masking composition. The liquid formulations including cevimeline hydrochloride may be administered to a patient to alleviate dry mouth symptoms associated with xerostomia and Sjogren's syndrome.

21 Claims, 1 Drawing Sheet

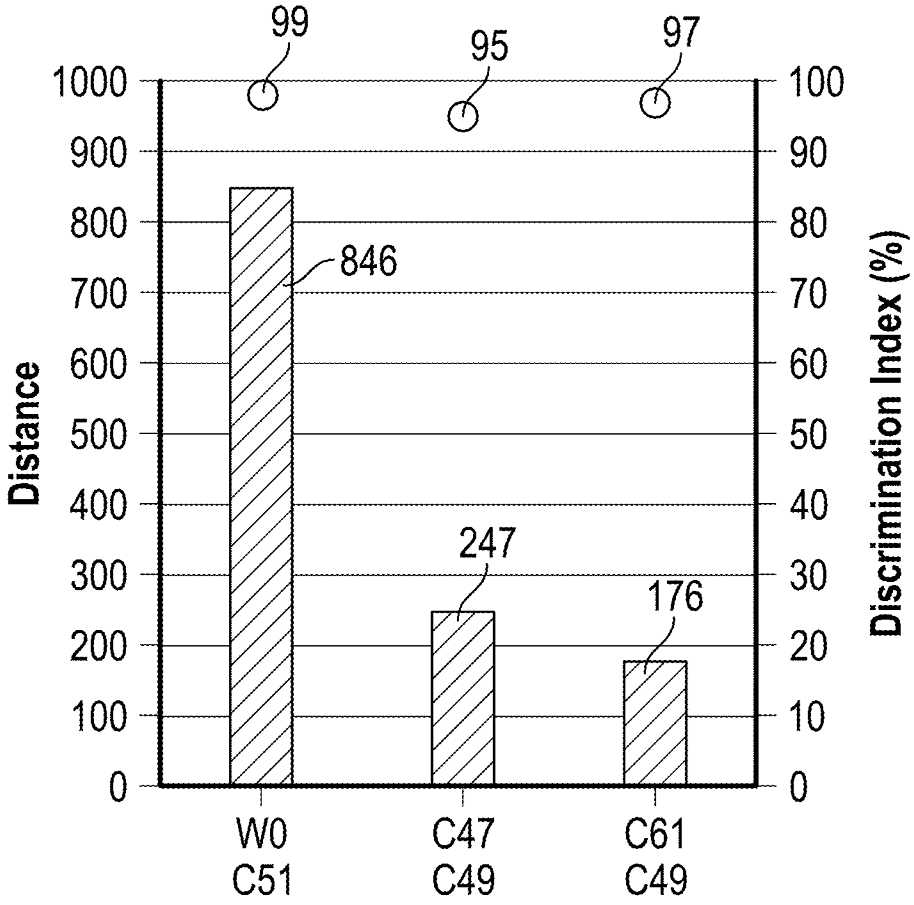
99
95
97
846
247
176
Distance
Discrimination Index (%)
0
100
200
300
400
500
600
700
800
900
1000
0
10
20
30
40
50
60
70
80
90
100
W0
C51
C47
C49
C61
C49

CEVIMELINE LIQUID FORMULATIONS

CROSS-REFERENCE TO RELATED APPLICATIONS

This application claims priority to U.S. Provisional Application No. 63/677,165 filed Jul. 30, 2024, the contents of which is incorporated herein by reference in its entirety.

FIELD OF THE INVENTION

The present disclosure generally relates to liquid formulations of cevimeline configured for oral administration and methods of treating xerostomia using such cevimeline liquid formulations.

BACKGROUND

Xerostomia, commonly referred to as dry mouth, is a condition characterized by reduced or absent saliva flow. This condition may result from various causes, including autoimmune diseases such as Sjögren's syndrome, medications, radiation therapy, or other medical conditions. Saliva plays a critical role in oral health, aiding in digestion, maintaining mucosal integrity, and preventing dental caries and infections. Accordingly, effective management of dry mouth is essential for improving patient quality of life and preventing further oral health complications.

Cevimeline is a pharmaceutical agent that is commonly prescribed for the treatment of xerostomia. It acts by stimulating the muscarinic receptors in exocrine glands, particularly the M1 and M3 receptor subtypes, thereby promoting increased glandular secretions, including saliva. Cevimeline is classified as a muscarinic receptor agonist (MRA) and is approved by the United States Food and Drug Administration (FDA) for the treatment of dry mouth associated with Sjögren's syndrome.

Currently, cevimeline is commercially available primarily in the form of solid oral dosage capsules. While effective, the solid capsule form may pose challenges for certain patient populations, particularly those with difficulty swallowing, which is a common symptom experienced by individuals suffering from xerostomia. As a result, there is a recognized need for alternative formulations of cevimeline that are more suitable for patients with swallowing difficulties.

In particular, liquid oral formulations of cevimeline would offer a more patient-friendly mode of administration, potentially improving treatment adherence and therapeutic outcomes. However, cevimeline is known to have a very bitter taste, which makes such alternative formulations less palatable and would negatively impact patient adherence.

SUMMARY

The present disclosure provides stable, palatable, liquid formulations of cevimeline configured for oral administration. The formulations effectively mask the bitter taste of the cevimeline hydrochloride, thus providing methods for the treatment of xerostomia that may improve treatment adherence and therapeutic outcomes.

An exemplary formulation of the present disclosure includes cevimeline hydrochloride, at least one sweetener, and at least one flavoring agent. Another exemplary formulation includes cevimeline hydrochloride and a novel taste masking composition.

An exemplary method of the present disclosure for treating xerostomia includes orally administering a liquid formulation including cevimeline hydrochloride, at least one sweetener, and at least one flavoring agent, or a liquid formulation including cevimeline hydrochloride and a novel taste masking composition.

BRIEF DESCRIPTION OF THE DRAWINGS

FIG. 1 demonstrates the overall taste comparison between (i) purified water (WO) and cevimeline hydrochloride in purified water (C51), (ii) a formulation absent cevimeline (C49) and a liquid formulation of the present disclosure (C47), and (iii) the formulation absent cevimeline (C49) and another liquid formulation of the present disclosure (C61) using CPS and NMS sensors of an electronic tongue.

DETAILED DESCRIPTION

Stable, palatable, liquid formulations of cevimeline configured for oral administration are provided, as well as use of the formulations in methods for the treatment of xerostomia that may improve treatment adherence and therapeutic outcomes.

Before the formulations and methods of the present disclosure are described, it is to be understood that both the foregoing summary and drawing, and the following detailed description may be exemplary and may not be restrictive of the aspects of the present disclosure as claimed. Certain details may be set forth to provide a better understanding of various features, aspects, and advantages of the invention. However, one skilled in the art will understand that these features, aspects, and advantages may be practiced without these details and/or in the absence of details not described herein. In other instances, well-known structures, methods, and/or processes associated with methods of practicing the various features, aspects, and advantages may not be shown or described in detail to avoid unnecessarily obscuring descriptions of other details of the invention.

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as would be understood by a person of ordinary skill in the art.

Definitions

In this description and in the appended claims, use of the singular forms "a", "an", and "the" includes the plural and plural encompasses singular, unless specifically stated otherwise. For example, although reference is made herein to "a" formulation, "an" antioxidant, or "the" sweetener, one or more of any of these components and/or any other components described herein may be used.

Likewise, as used herein, a term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances.

Various aspects may be described and illustrated with reference to one or more exemplary implementations. As used herein, the term "exemplary" means "serving as an example, instance, or illustration," and should not necessarily be construed as preferred or advantageous over other variations of the compositions and aspects disclosed herein. "Optional" or "optionally" means that the subsequently described event or circumstance may or may not occur, and that the description includes instances where the implementation occurs and instances where it does not.

As used herein, the term "aspect" may be understood to mean a particular part or feature of the disclosed invention, wherein the present disclosure relates to any combination of the disclosed aspects.

The word "comprising" and forms of the word "comprising", as used in this description and in the claims, does not limit the present disclosure to exclude any variants or additions. Additionally, although the present disclosure has been described in terms of "comprising", the processes, materials, and compositions detailed herein may also be described as consisting essentially of or consisting of. For example, while certain aspects of the present disclosure have been described in terms of a liquid formulation comprising cevimeline and certain other components (e.g., sweeteners, flavoring agents, an antioxidant), a liquid formulation "consisting essentially of" or "consisting of" cevimeline and any of these other components is also within the present scope. In this context, "consisting essentially of" means that any additional components will not materially affect the efficacy or the taste or palatability of the liquid formulation or method of use thereof.

Moreover, other than in the examples, or where otherwise indicated, all numbers expressing, for example, quantities of ingredients used in the specification are to be understood as being modified in all instances by the term "about," wherein the term "about" indicates approximations which may vary by ±10%, ±5%, or ±1%. Accordingly, unless indicated to the contrary, the numerical parameters set forth in the following specification are approximations that may vary depending upon the desired properties to be obtained by the present disclosure (e.g., temperature, time, amount, and concentration, including ranges). At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the present disclosure are approximations and reported as precisely as possible, any numerical value inherently contains certain errors necessarily resulting from the standard variation found in their respective testing measurements. The numerical parameters provided in the examples section of this disclosure are reported with as much precision as possible. Precision refers to the degree to which repeated measurements or outputs under unchanged conditions yield the same or consistent results. In the context of the present disclosure, "precision" characterizes the repeatability or reproducibility of a given process, measurement, or system function, independent of its accuracy relative to a standard or target value. Higher precision indicates lower variability or deviation among measurements or outcomes under identical conditions.

When ranges are given, any endpoints of those ranges and/or numbers within those ranges can be combined within the scope of the present disclosure.

As used herein, the term "sweetener" or "sweetening agent" refers to any compound that provides a sweet taste and/or may make the product more palatable. This may include, but is not limited to, sugars, natural and artificial sweeteners, natural extracts, and any material that initiates a sweet sensation in a subject.

As used herein, the term "flavoring agent" or "flavorant" refers to any component that enhances or imparts a particular taste or aroma in a product.

As used herein, the term "taste masking agent" refers to any component used to disguise the bitter or unpleasant taste of active ingredients in medications.

As used herein, "sugars" may include natural and synthetic sugars, including, but not limited to, glucose, fructose, sucrose, xylitol, tagatose, maltitol, isomaltulose, lactitol, sorbitol, mannitol, erythritol, trehalose, maltodextrin, polydextrose, aspartame, sucralose, stevia, steviol, stevioside, rebaudioside A, and the like.

As used herein, "coloring agent" may include any agent that aids in the color identification or enhances aesthetics of the liquid formulations of the present disclosure. A coloring agent may include, but is not limited to, any coloring agent approved by the U.S. Food and Drug Administration (FDA), including, but not limited to, FD&C Red No. 3, FD&C Red No. 20, FD&C Red No. 40, FD&C Yellow No. 6, FD&C Blue No. 2, FD&C Green No. 5, FD&C Orange No. 5, FD&C Yellow No. 10, caramel, ferric oxide, and mixtures thereof. The term "coloring agent" may also refer to any food grade naturally derived coloring agent, such as derived from carrots, turmeric, beetroot, cabbage, berries, flowers, and the like. The liquid formulations of the present disclosure may optionally include one or more coloring agents.

As used herein, "viscosity" refers to the internal friction that occurs from the molecules within a liquid. Viscosity is a measure of the resistance to deformation in shear, such as flow or pouring, and is caused by the intermolecular friction and molecular adhesion-cohesion within the fluid. Exemplary viscosities for oral formulations include at least 2 cP to 10,000 cP, such as 10 cP to 2000 cP, or 25 cP to 1500 cP, or 40 cP to 300 cP, or 50 cP to 150 cP, or 50 cP to 130 cP measured at ambient temperature (e.g., 17-25° C.). Exemplary viscosities for oral formulations comprising cevimeline of the present disclosure include 40 cP to 300 cP, or 50 cP to 150 cP, or 50 cP to 130 cP, or 60 cP to 120 cP, or 70 cP to 110 cP, measured at ambient temperature (e.g., 17-25° C.). Methods for measuring viscosity of fluids are well known in the art.

As used herein, the term "glycerin" is used interchangeably with the term "glycerol", wherein "glycerol" is typically used in a pure or mixed form, and "glycerin" is the commercial name of "glycerol", which may or may not be pure and comprises at least 90% of glycerol. There is no chemical difference between glycerol and glycerin, except for various levels of purity.

As used herein, the term "shelf-life" refers to the time period over which the product maintains its potency, efficacy and physical characteristic within acceptable limits.

The term "stable" as used in the present disclosure relates to both chemical stability (shelf-life) and physical stability (suspension uniformity).

As used herein, "chemically stable" in reference to a formulation of the present disclosure describes a composition that is resistant to decomposition when exposed to natural conditions, such as air, heat, light, pressure, or humidity for a period of time. In some aspects, the period of time may be more than one week or more than two weeks or more than three weeks or more than four weeks or more than one month or more than two months or more than three months or more than four months or more than five months or more than six months. In some non-limiting examples, a chemically stable liquid formulation is resistant to decomposition when exposed to air, heat, light, pressure, or humidity for more than one week or more than two weeks or more than three weeks or more than four weeks or more than one month or more than two months or more than three months or more than four months or more than five months or more than six months.

Formulations of the present disclosure exhibit good storage stability, meaning that the materials do not lose their desirable properties during storage for a specified time period, i.e., are chemically stable. Preferred formulations do not exhibit an increase in impurities of more than 1% w/v, or more than 0.8% w/v, or 0.6% w/v, or 0.5% w/v, or 0.4% w/v, or 0.3% w/v or 0.2% w/v, or even 0.1% w/v during storage, such as during periods of time in which the formulations are considered to be stable.

The various components of the disclosed liquid formulations are mutually compatible, i.e., exhibit good physical stability. Mutual compatibility of the components means that the components do not separate in preparation and storage for up to the equivalent of two years at room temperature (as indicated by three-month intervals of accelerated stability testing at 40° centigrade and at 75% relative humidity).

As used herein, "cevimeline" and "cevimeline hydrochloride" are used interchangeably. However, other formulations of cevimeline (including salts other than hydrochloride) are possible and within the scope of the present disclosure.

As used herein, the term "bitter" or derivatives thereof (e.g. "bitterness") refers to an undesirable, sensory experience of taste perceived by a subject or measured using a sensor, such as an electronic tongue (e-tongue) sensor. As a non-limiting example, a substance may be considered bitter if the substance is perceived by the subject as unpleasant, sharp, astringent or harsh on the palate. Methods for determining a bitterness level include at least an e-tongue assay. In an e-tongue assay, a "discrimination index" is measured, which refers to a metric used to quantify how well the sensor array can differentiate between different samples, essentially indicating the degree of separation between various taste profiles detected by the e-tongue (e.g., sourness, saltiness, umami, etc.). The discrimination index is usually expressed as a percentage and calculated based on statistical analysis of the sensor responses, often using techniques like Principal Component Analysis (PCA).

As used herein, "treatment," "treating," and the like generally mean obtaining a desired pharmacological and physiological effect. The effect may be prophylactic in terms of preventing or partially preventing a disease, symptom or condition thereof, e.g., prevent dry mouth or xerostomia, and/or may be therapeutic in terms of a partial or complete cure of a symptom or adverse effect attributed to the disease, e.g., cure dry mouth or xerostomia. The term "treatment" as used herein covers any treatment of a disease, condition, symptom, or adverse effect (e.g., treat dry mouth, xerostomia, or symptoms of Sjogren's syndrome) in a mammal, particularly a human, and includes: a) preventing the disease, condition, symptom, or adverse effect from occurring in a subject that may be a predisposed condition, symptom or adverse effect but has not yet been diagnosed as having it such as a preventive early asymptomatic intervention; b) inhibiting the disease, condition, symptom, or adverse effect, i.e., arresting its development; or c) relieving the disease, condition, symptom, or adverse effect, i.e., causing regression of disease, condition, symptom, or adverse effect such as improvement or remediation of damage.

The term "effective amount" as used herein refers to an amount of at least one compound of the present disclosure or a pharmaceutical formulation thereof according to the present disclosure that elicits the biological or medicinal response in a tissue, system, animal or human that is being sought, e.g., partially or completely prevent, cure, or treat dry mouth, xerostomia, Sjogren's syndrome or symptoms thereof. In one aspect, the effective amount is a "therapeutically effective amount" for the alleviation of symptoms of the disease or condition being treated. In another aspect, the effective amount is a "prophylactically effective amount" for prophylaxis of the symptoms of the disease or condition being prevented. The term also includes an amount of the compound of the present disclosure useful to reduce the progression of the disease, condition, symptom, or adverse effect, notably to reduce or inhibit the progression of a disorder and thereby elicit the response being sought (i.e. an "effective amount"). An "effective amount" may vary according to factors such as the disease state, age, gender, and weight of the individual, and the ability of a therapeutic or a combination of therapeutics to elicit a desired response in the individual. Exemplary indicators of an effective amount include, for example, improved well-being of the patient, and reduction in dry mouth and/or an increase in saliva production.

As used herein, "administer" means to deliver a composition comprised of a predetermined drug dosage by oral administration.

"Patient" or "subject" includes any human or nonhuman animal. "Nonhuman animal" includes all vertebrates, e.g., mammals and non-mammals, such as nonhuman primates, cattle, sheep, pigs, dogs, cats, horses, cows, laboratory rodents, chickens, amphibians, reptiles, other pets, and the like. "Patient" and "subject" are used interchangeably herein.

Formulations and Methods of the Present Disclosure

Oral administration of solid capsules or pills in patients suffering from dry mouth or xerostomia is often difficult, ineffective, or not possible. Many patients with xerostomia report difficulty swallowing, negatively impacting quality of life and the ability to swallow solid capsules. This may lead to patient non-compliance with the solid oral dosage forms and likely results in rendering the treatment ineffective. Moreover, solid oral dosage forms are particularly unfavorable for pediatric and geriatric patient populations, as there is an increased risk of choking.

Cevimeline hydrochloride is a drug commonly prescribed to treat dry mouth or xerostomia in patients with Sjogren's syndrome. Cevimeline is cis-2'-methylspiro {1-azabicyclo [2.2.2]octane-3, 5'-[1,3]oxathiolane}hydrochloride, hydrate (2:1). Its empirical formula is $C_{10}H_{17}NOS \cdot HCl \cdot \frac{1}{2}H_2O$, and its structural formula is:

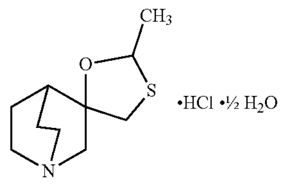

Cevimeline hydrochloride is commercially available in the form of oral capsules (e.g., Evoxac® and also generic). Solid oral administration of cevimeline may result in oral discomfort, dysphagia, nausea, and vomiting. Currently, there is no commercially available oral liquid formulation of cevimeline hydrochloride to treat dry mouth or xerostomia that may be used for all populations and various indications. The lack of commercial availability may be attributed to the bitter taste of cevimeline hydrochloride liquid formulations, as patients are less likely to comply with self-administering bitter oral liquids. Accordingly, there is an unmet need for alternative cevimeline administration modes that address one or more of the aforementioned shortcomings of solid administration.

The present disclosure provides a novel cevimeline hydrochloride liquid formulation for oral administration that mitigates the bitterness and enhances oral administration. The present disclosure utilizes a unique combination of one or more of a sweetener and a flavoring agent, i.e., a taste masking composition, to overcome the difficulties arising from prior art methods of administering cevimeline hydrochloride.

Thus, the present disclosure provides liquid compositions including cevimeline hydrochloride as the active ingredient, and a novel taste masking composition comprising one or more of each of a sweetener and a flavoring agent. The liquid compositions may include one or more additional active ingredients depending on the condition(s) to be treated. Moreover, while cevimeline hydrochloride is described herein, other forms of cevimeline that are known in the art are possible and within the scope of the present disclosure.

The liquid formulations of the present disclosure may include additional ingredients, including, but not limited to, solvents, cosolvents, buffering agents, preservatives, and/or antioxidants. The liquid formulations of the present disclosure may include further additional ingredients, including, but not limited to, coloring agents, viscosity builders, chelating agents, solubilizers, and/or pharmaceutically acceptable salts.

Cevimeline Hydrochloride

The liquid formulations of the present disclosure include cevimeline, e.g., cevimeline hydrochloride, in amounts of at least 0.10% w/v to 1.0% w/v cevimeline hydrochloride, including, but not limited to, at least 0.10% w/v, 0.15% w/v, 0.20% w/v, 0.30% w/v, 0.50% w/v, 0.60% w/v, 0.75% w/v, 0.80% w/v, and at least 1.0% w/v. The cevimeline hydrochloride may be present in an amount of not more than 1.0% w/v, including, but not limited to, not more than 1.0% w/v, 0.80% w/v, 0.75% w/v, 0.60% w/v, 0.50% w/v, 0.30% w/v, 0.20% w/v, 0.15% w/v, and not more than 0.10% w/v. Any combination of upper and lower limits are possible and within the scope of the present disclosure, including, but not limited to, 0.10% w/v to 0.15% w/v, 0.10% w/v to 0.30% w/v, 0.10% w/v to 0.60% w/v, 0.30% w/v to 0.60% w/v, 0.3% w/v to 1.0% w/v, 0.50% w/v to 1.0% w/v, 0.4% w/v to 0.8% w/v, 0.60% w/v to 1.0% w/v, and 0.60% w/v based on the total volume of the liquid formulation.

One of ordinary skill in the art may readily determine the appropriate concentration, or dose, of cevimeline hydrochloride. The skilled artisan will recognize that a preferred dose is one which produces a therapeutic effect, such as increasing salivary gland production in the mouth. Proper doses of cevimeline and dosing regimens are determined by one of skill in the art and may be determined at the time of use based on several variables, including, but not limited to, patient age, weight, gender, health; other medications and treatments being administered to the patient; and the like. As a non-limiting example, cevimeline hydrochloride may be administered in 30 mg/5 ml doses.

Sweeteners

The liquid formulations may include one or more sweeteners configured to provide a sweet taste to make the product more palatable. As a non-limiting example, a liquid formulation may include at least 1, 2, 3, 4, 5, 6, or at least 7 sweeteners. A sweetener may include, but is not limited to, sugars, sugar alcohols, polyols, glucose, fructose, sucrose, xylitol, tagatose, sucralose, maltitol, isomaltulose, lactitol, sorbitol, sorbitol solution (1% to 90% w/v sorbitol in water), sugar substitutes, artificial sweeteners, stevia leaf extract, stevia, corn syrup, honey, aspartame, mannitol, erythritol, trehalose, maltodextrin, polydextrose, glycerin, inulin, acesulfame and salts thereof, acesulfame potassium, alitame, neotame, sodium cyclamate, saccharin, saccharin sodium, saccharin calcium, neohesperidin dihydrochalcone, stevioside, thaumatin, combinations thereof, and the like. A sweetener may include, but is not limited to, crude or refined products such as hydrogenated starch hydrolysates, maltitol syrup, high fructose corn syrup, and branded proprietary blend products.

The one or more sweeteners may be present in an amount of 0.01% w/v to 40.0% w/v. The one or more sweeteners may be present in an amount of at least 0.01% w/v, including, but not limited to, at least 0.01% w/v, 0.05% w/v, 0.10% w/v, 0.50% w/v, 1.0% w/v, 2.0% w/v, 5.0% w/v, 7.5% w/v, 10.0% w/v, 15.0% w/v, 20.0% w/v, 25.0% w/v, 30.0% w/v, 35.0% w/v, and at least 40.0% w/v. The one or more sweeteners may be present in an amount not more than 40.0% w/v, including, but not limited to, not more than 40.0% w/v, 35.0% w/v, 30.0% w/v, 25.0% w/v, 20.0% w/v, 15.0% w/v, 10.0% w/v, 7.5% w/v, 5.0% w/v, 2.0% w/v, 1.0% w/v, 0.5% w/v, 0.10% w/v, 0.05% w/v, and not more than 0.01% w/v. Any combination of upper and lower limits are possible and within the scope of the present disclosure, including, but not limited to, 0.01% w/v to 0.05% w/v, 0.05% w/v to 0.10% w/v, 0.10% w/v to 0.50% w/v, 0.50% w/v to 1.0% w/v, 0.1% w/v to 2.0% w/v, 1.0% w/v to 2.0% w/v, 1.0% w/v to 10% w/v, 5% w/v to 10% w/v, 5% w/v to 15% w/v, 10% w/v to 15% w/v, 1.0% w/v to 15% w/v, 0.5% w/v to 20% w/v, 1.0% w/v to 20% w/v, 2.0% w/v to 15.0% w/v, 1.0% w/v to 16.0% w/v, 4% w/v to 18% w/v, 5% w/v to 20% w/v, and 15.0% w/v to 40.0% w/v.

In an exemplary formulation, the one or more sweeteners comprise sucralose and sorbitol, such as about 0.5% w/v to 1.5% w/v sucralose and 5% w/v to 20% w/v sorbitol, such as 5% w/v to 15% w/v of a 70% solution of sorbitol. Another exemplary formulation comprises 5% w/v to 17% w/v of the one or more sweetener, such as 0.5% w/v to 2.0% w/v of sucralose and 5% w/v to 15% w/v of a 70% solution of sorbitol. In another exemplary formulation, the one or more sweeteners comprise sucralose and sorbitol, such as about 0.8% w/v to 1.2% w/v sucralose and 8% w/v to 12% w/v of a 70% solution of sorbitol.

Flavoring Agents

The liquid formulations may include one or more flavoring agents. As a non-limiting example, a liquid formulation may include at least 1, 2, 3, 4, 5, 6, or at least 7 flavoring agents. A flavoring agent may be natural or artificial and may be used to improve the sensory experience of a product by providing characteristic flavors such as fruit, spice, or savory profiles. A flavoring agent may be in the form of liquids, powders, extracts. One or more flavoring agents may be selected and formulated to achieve a desired taste and aroma while meeting safety and regulatory requirements. Non-limiting examples of natural or artificial flavors, some of which may be simulated with synthetic agents or combinations thereof, include almond, anise, apple, apricot, banana, blackberry, blackcurrant, blueberry, caramel, cherry, chocolate, cinnamon, cranberry, grape, lemon, lime, orange, peppermint, pineapple, raspberry, spearmint, strawberry, vanilla, and the like. Flavoring agents may include branded proprietary products, bubble gum flavor, or a compounded flavoring agent based on fruit flavors. Flavoring agents may be used singly or in combinations of two or more.

The liquid formulations of the present disclosure may include one or more flavoring agents with masking like flavor character when present in a solution containing a bitter active ingredient such as cevimeline, i.e., taste masking agents. Exemplary taste masking agents include at least maltol, ethyl maltol, 5-hydroxymaltol.

The one or more flavoring agents may be present in an amount of 0.001% w/v to 5.0% w/v. The one or more flavoring agents may be present in an amount of at least 0.001% w/v, including, but not limited to, at least 0.001% w/v, 0.005% w/v, 0.01% w/v, 0.05% w/v, 0.10% w/v, 0.15% w/v, 0.20% w/v, 0.25% w/v, 0.50% w/v, 0.75% w/v, 1.0% w/v, 2.0% w/v, 3.0% w/v, 4.0% w/v, and at least 5.0% w/v. The one or more flavoring agents may be present in an amount of not more than 5.0% w/v, including, but not limited to, not more than 5.0% w/v, 4.0% w/v, 3.0% w/v, 2.0% w/v, 1.0% w/v, 0.75% w/v, 0.50% w/v, 0.25% w/v, 0.20% w/v, 0.15% w/v, 0.10% w/v, 0.05% w/v, 0.005% w/v, and not more than 0.001% w/v. Any combination of upper and lower limits are possible and within the scope of the present disclosure, including, but not limited to, 0.001% w/v to 0.05% w/v, 0.05% w/v to 0.10% w/v, 0.001% w/v to 0.10% w/v, 0.001% w/v to 0.50% w/v, 0.50% w/v to 1.0% w/v, 0.25% w/v to 0.75% w/v, 0.10% w/v to 0.75% w/v, 0.10% w/v to 1.0% w/v, 1.0% w/v to 2% w/v, 0.10% w/v to 3% w/v, 0.10% w/v to 5.0% w/v, 0.05% w/v to 5.0% w/v, 0.01% w/v to 5.0% w/v, 0.01% w/v to 4.0% w/v, 0.01% w/v to 3.0% w/v, and 1.0% w/v to 5.0% w/v.

In an exemplary formulation, the one or more flavoring agents may comprise a natural or artificial flavoring agent, such as a fruit flavoring agent, and a taste masking agent, such as maltol. For example, the natural or artificial fruit flavoring agent and the taste masking agent may be included in the formulation at 0.1% w/v to 0.75% w/v. In another exemplary formulation, the one or more flavoring agents may comprise a natural or artificial fruit flavoring agent, included in the formulation at 0.05% w/v to 0.25% w/v, and maltol included in the formulation at 0.01% w/v to 0.05% w/v. In yet another exemplary formulation, the one or more flavoring agents may comprise a natural or artificial fruit flavoring agent, included in the formulation at 0.01% w/v to 0.25% w/v, and a taste masking agent such as maltol included in the formulation at 0.01% w/v to 0.03% w/v.

Taste Masking Compositions

Certain flavoring agents may be considered both a sweetener and a flavoring agent. A sweetener and a flavoring agent may act to disguise the bitter or unpleasant taste of active ingredients in medications. For example, in the absence of the one or more sweeteners and flavoring agents of the disclosed formulations, cevimeline hydrochloride liquid compositions have an unpleasant, bitter taste. Thus, the present disclosure provides a novel taste masking composition that is a combination of the one or more sweeteners and one or more flavoring agents discussed hereinabove. The taste masking compositions improve palatability of the disclosed liquid formulations of cevimeline so that they are more tolerable and easier to administer for patients. The liquid formulations of the present disclosure that include the novel taste masking composition increase patient compliance compared to the prior art.

The taste masking compositions of the present disclosure that are included in the liquid formulations of cevimeline may include a novel combination of at least one sweetener and at least one flavoring agent, wherein the combination may include, but is not limited to, at least 1, 2, 3, 4, 5, 6, 7, 8, 9, and 10 sweeteners, and at least 1, 2, 3, 4, 5, 6, 7, 8, 9, and 10 flavoring agents. As a non-limiting example, the liquid formulation may include a two or more sweeteners and two or more taste masking agents. For example, the taste masking compositions may comprise sucralose, sorbitol, an artificial flavor, and maltol to mask the bitter taste of the active ingredient.

The liquid formulations of the present disclosure may include a ratio of sweetener to flavoring agent, including, but not limited to, 5 to 15% w/v sweetener to 0.05 to 0.25% w/v flavoring agent, based on the total volume of the formulation.

The taste masking compositions of the present disclosure may include a ratio of sweetener to flavoring agent, including, but not limited to: 500:1, 200:1, 100:1, 90:1, 80:1, 70:1, 60:1, 50:1, 40:1, 30:1, 20:1, 10:1, 5:1, 4:1, 3:1, or 2:1. The taste masking compositions of the present disclosure may include a range of ratios of sweetener to flavoring agent, including, but not limited to: 500:1 to 2:1, 200:1 to 20:1, 100:1 to 40:1, or 80:1 to 60:1.

The liquid formulations of the present disclosure of the present disclosure may include a ratio of sweetener to flavoring agent to cevimeline, including, but not limited to: 500:1:40, 200:1:40, 200:1:20, 200:1:15, 150:1:6, 100:1:40, 100:1:20, 100:1:10, 80:1:10, 80:1:6, 70:1:6, 60:1:4, 50:1:3, 40:1:6, 40:1:3, 30:1:2, 20:1:1, 15:1:1, 10:1:1, 5:1:1, 4:1:1, 3:1:1, or 2:1:1. The taste masking compositions of the present disclosure may include a range of ratios of sweetener to flavoring agent to cevimeline, including, but not limited to: 500:1:40 to 8:1:1, 200:1:20 to 40:1:6, 100:1:10 to 40:1:6, or 150:1:6 to 15:1:1.

The liquid formulations of the present disclosure may include a ratio of sweetener to cevimeline, including, but not limited to 10:1, 50:10, 50:3, 30:1, 20:1, or 18:1. The liquid formulations of the present disclosure may include a range of ratios of sweetener to cevimeline, including, but not limited to 60:1 to 5:1, 40:1 to 10:1, 30:1 to 10:1, 25:1 to 15:1, or 20:1 to 15:1.

The liquid formulations of the present disclosure may include a ratio of flavoring agent to cevimeline, including, but not limited to 1:50, 1:40, 1:30, 1:20, 1:10, 1:5, 1:2, or 1:1. The liquid formulations of the present disclosure may include a range of ratios of flavoring agent to cevimeline, including, but not limited to 1:50 to 1:1, 1:40 to 1:5, 1:30 to 1:10, 1:10 to 1:4, or 1:8 to 1:4.

Solvents

Primary solvents suitable for cevimeline hydrochloride liquid formulations may depend upon the type of desired oral liquid composition (e.g., solution, suspension, etc.), as well as other properties including, but not limited to, clarity, viscosity, compatibility with excipients, chemical inertness, palatability, odor, and color. Non-limiting examples of primary solvents include, but are not limited to, water, purified water, juices (e.g., apple, orange, cranberry, cherry, tomato, and the like), other beverages (e.g., tea, coffee, soft drinks, milk, and the like), oils (e.g., olive, soybean, corn, mineral, castor, and the like), and combinations or mixtures thereof. Certain primary solvents, e.g. water and oil, may be combined together to form emulsions. In some aspects, water or purified water is the primary solvent.

The primary solvent may be present in at least 15% to 99.99% w/v. The primary solvent may be at least 15% w/v, including but not limited to, 15% w/v, 20% w/v, 25% w/v, 30% w/v, 35% w/v, 40% w/v, 45% w/v, 50% w/v, 55% w/v, 60% w/v, 65% w/v, 70% w/v, 75% w/v, 80% w/v, 85% w/v, 90% w/v, 95% w/v, 97% w/v, 99% w/v, 99.9% w/v, and least 99.99% w/v. The primary solvent may be not more than 99.99% w/v, including, but not limited to, not more than 99.99% w/v, 99.9% w/v, 99% w/v, 98% w/v, 97% w/v, 95% w/v, 90% w/v, 85% w/v, 80% w/v, 75% w/v, 70% w/v, 65% w/v, 60% w/v, 55% w/v, 50% w/v, 45% w/v, 40% w/v, 35% w/v, 30% w/v, 25% w/v, 20% w/v, and not more than 15% w/v. Any combination of the lower and upper limits is within the scope of the present disclosure, including, but not limited to, 15% w/v to 20% w/v, 25% w/v to 35% w/v, 40% w/v to 50% w/v, 50% w/v to 60% w/v, 55% w/v to 65% w/v, 60% w/v to 65% w/v, 60% w/v to 80% w/v, 70% w/v to 90% w/v, and 90% w/v to 99.99% w/v. Water may be added to the formulation quantum satis to achieve the desired formulation. As a non-limiting example, water may be added until the desired final volume or dosage is achieved.

The liquid formulations may include one or more cosolvents or secondary solvents that do not react with the primary solvent but may increase the solubility of a poorly soluble compound, improve the solubility from non-miscible phases, and/or improve oral bioavailability of an active compound or ingredient. Cosolvents may include, but are not limited to, glycerin, glycerol, glycols, propylene glycol, ethanol, glycofural, dimethyl sulfoxide (DMSO), benzyl alcohol, solid lipid nanoparticles, nanostructured lipid carriers, nano-emulsions, self-emulsifying drug delivery systems, and the like.

The one or more cosolvents may be present in an amount of 1.0% w/v to 50.0% w/v. The one or more cosolvents may be present in an amount of at least 1.0% w/v, including, but not limited to, at least 1.0% w/v, 5.0% w/v, 10.0% w/v, 15.0% w/v, 20.0% w/v, 25.0% w/v, 30.0% w/v, 35.0% w/v, 40.0% w/v, 45.0% w/v, and at least 50.0% w/v. The one or more cosolvents may be present in an amount not more than 50.0% w/v, including, but not limited to, not more than 50.0% w/v, 45.0% w/v, 40.0% w/v, 35.0% w/v, 30.0% w/v, 25.0% w/v, 20.0% w/v, 15.0% w/v, 10.0% w/v, 5.0% w/v, and not more than 1.0% w/v. Any combination of upper and lower limits are possible and within the scope of the present disclosure, including, but not limited to, 1.0% w/v to 5.0% w/v, 5.0% w/v to 10.0% w/v, 5.0% w/v to 15.0% w/v, 15.0% w/v t 25.0% w/v, 20.0% w/v to 30.0% w/v, 30.0% w/v to 40.0% w/v, and 40.0% w/v to 50.0% w/v.

In an exemplary formulation, the solvent may be included at 60% w/v to 90% w/v. In an exemplary formulation, the solvent comprises water, glycerin, and propylene glycol, such as 50% w/v to 70% w/v water, 10% w/v to 20% w/v glycerin, and 5% w/v to 15% w/v propylene glycol. In another exemplary formulation, the solvent comprises 10% w/v to 20% w/v glycerin, 5% w/v to 15% w/v propylene glycol, and water added quantum satis to achieve the desired formulation.

Buffering Agents

The liquid formulations may include one or more buffering agents that maintain the pH of cevimeline hydrochloride liquid formulations. Buffering agents include, but are not limited to, sodium bicarbonate, potassium bicarbonate, magnesium hydroxide, magnesium lactate, citric acid, anhydrous citric acid, acetic acid, sodium acetate, sodium citrate, sodium citrate dihydrate, magnesium gluconate, aluminum hydroxide, aluminum hydroxide/sodium bicarbonate precipitate, a mixture of an amino acid and a buffer, a mixture of an acid salt and an amino acid and a buffer, a mixture of aluminum glycinate and a buffer, a mixture of an alkali salt of an amino acid and a buffer, sodium carbonate, sodium tartrate, sodium polyphosphate, potassium polyphosphate, sodium pyrophosphate, potassium pyrophosphate, disodium hydrosodium acetate, potassium metaphosphate, magnesium oxide, magnesium carbonate, magnesium silicate, calcium acetate, calcium glycerophosphate, calcium chloride, calcium hydroxide, calcium lactate, calcium carbonate, calcium bicarbonate, other calcium salts, combinations thereof, and the like. A buffering agent may include any compound that adjusts pH, including, but not limited to, sodium hydroxide, hydrochloric acid, any of the compounds discussed herein, and any combination thereof.

The one or more buffering agents may be present in an amount of at least 0.05% w/v to 1% w/v. The one or more buffering agents may be present in an amount of at least 0.05% w/v, including, but not limited to, 0.05% w/v, 0.10% w/v, 0.15% w/v, 0.20% w/v, 0.25% w/v, 0.30% w/v, 0.35% w/v, 0.40% w/v, 0.45% w/v, 0.50% w/v, 0.55% w/v, 0.60% w/v, 0.65% w/v, 0.70% w/v, 0.75% w/v, 0.80% w/v, 0.85% w/v, 0.90% w/v, 0.95% w/v, and at least 1.0% w/v, The one or more buffering agents may be present in an amount not more than 1.0% w/v, including, but not limited to, 1.0% w/v, 0.95% w/v, 0.90% w/v, 0.85% w/v, 0.80% w/v, 0.75% w/v, 0.70% w/v, 0.65% w/v, 0.60% w/v, 0.55% w/v, 0.50% w/v, 0.45% w/v, 0.40% w/v, 0.35% w/v, 0.30% w/v, 0.25% w/v, 0.20% w/v, 0.15% w/v, 0.10% w/v, and not more than 0.05% w/v. Any combination of upper and lower limits are possible and within the scope of the present disclosure, including, but not limited to, 0.05% w/v to 0.10% w/v, 0.10% w/v to 0.15% w/v, 0.20% w/v to 0.25% w/v, 0.35% w/v to 0.45% w/v, 0.55% w/v to 0.65% w/v, 0.60% w/v to 0.65% w/v, 0.50% w/v to 0.80% w/v, 0.55% w/v to 0.75% w/v, and 0.75% w/v to 1.0% w/v.

The liquid formulations of the present disclosure may have a pH of at least 2.0, including, but not limited to, at least 2.0, 2.5, 3.0, 3.5, 4.0, 4.5, 5.0, 5.5, 6.0, 6.5, 7.0, 7.5, and at least 8.0. The pH may be not more than 8.0, including, but not limited to, no more than 8.0, 7.5, 7.0, 6.5, 6.0, 5.5, 5.0, 4.5, 4.0, 3.5, 3.0, 2.5, and not more than 2.0. Any combination of the lower and upper limits is within the scope of the present disclosure, including, but not limited to, a pH of 2.0 to 3.0, 2.0 to 4.0, 2.0 to 5.0, 2.0 to 6.0, 2.0 to 8.0, 4.0 to 6.0, 4.0 to 8.0, 4.0 to 5.0, 4.5 to 5.0 5.0 to 6.0, 3.0 to 4.0, 3.0 to 5.0, 3.0 to 6.0, and 3.0 to 8.0.

In an exemplary formulation, the buffering agent comprises include anhydrous citric acid and sodium citrate dihydrate, such as 0.2% w/v to 0.25% w/v citric acid and 0.35% w/v to 0.45% w/v sodium citrate. According to certain preferred aspects, the liquid formulations of the present disclosure may have a pH of 3.0 to 7.0, such as 4.0 to 6.0, or 4.0 to 5.7, or 4.1 to 5.9, or 4.2 to 5.8, or 4.2 to 5.5, or 4.3 to 5.7 or 4.4 to 5.5, or 4.4 to 5.4, or 4.6 to 5.1, or 4.4 to 4.8.

Preservatives

The liquid formulations of the present disclosure may include one or more preservatives to prevent bacterial and fungal growth or contamination and/or to prevent undesirable chemical changes. Preservatives may include, but are not limited to, anti-microbials, agents that enhance sterility, ascorbyl palmitate, methylparaben, benzyl alcohol, citric acid, propylparaben, erythorbic acid, fumaric acid, malic acid, propyl gallate, sodium ascorbate, gluconic acid and salts, diethylene triamine penta-acetic acid (DTPA), phosphate and salts, hydroxycarboxylic acids, tartaric acid, ethylparaben, butylparaben, sodium bisulfate, sodium benzoate, benzoic acid, potassium sorbate, vanillin, combinations thereof, and the like.

The one or more preservatives may be present in an amount of 0.005% w/v to 5% w/v. The one or more preservatives may be present in an amount of at least 0.01% w/v, including, but not limited to, 0.005% w/v, 0.01% w/v, 0.02% w/v, 0.05% w/v, 0.10% w/v, 0.15% w/v, 0.20% w/v, 0.25% w/v, 0.50% w/v, 0.75% w/v, 1.0% w/v, 1.25% w/v, 1.50% w/v, 1.75% w/v, 2.0% w/v, 2.25% w/v, 2.50% w/v, 2.75% w/v, 3.0% w/v, 3.25% w/v, 3.5% w/v, 3.75% w/v, 4.0% w/v, 4.25% w/v, 4.5% w/v, 4.75% w/v, and at least 5.0% w/v. The one or more preservatives may be present in an amount not more than 3.0% w/v, including, but not limited to, not more than 5.0% w/v, 4.75% w/v, 4.5% w/v, 4.25% w/v, 4.0% w/v, 3.75% w/v, 3.5% w/v, 3.25% w/v, 3.0% w/v, 2.75% w/v, 2.50% w/v, 2.25% w/v, 2.0% w/v, 1.75% w/v, 1.50% w/v, 1.25% w/v, 1.0% w/v, 0.75% w/v, 0.50% w/v, 0.25% w/v, 0.20% w/v, 0.15% w/v, 0.10% w/v, 0.05% w/v, 0.02% w/v, and not more than 0.01% w/v. Any combination of upper and lower limits are possible and within the scope of the present disclosure, including, but not limited to, 0.01% w/v to 0.02% w/v, 0.1% w/v to 0.3% w/v, 0.01% w/v to 0.25% w/v, 0.10% w/v to 0.20% w/v, 0.15% w/v to 0.25% w/v, 0.20% w/v to 0.25% w/v, 0.25% w/v to 0.50% w/v, 0.5% w/v to 1.0% w/v, 1.0% w/v to 2.0% w/v, 0.01% w/v to 2.0% w/v, 0.05% w/v to 5.0% w/v, 0.01% w/v to 5.0% w/v, 0.05% w/v to 3.0% w/v, and 2.0% w/v to 3.0% w/v.

In an exemplary formulation, the preservatives include methylparaben and propylparaben, such as 0.1% w/v to 0.3% w/v methylparaben and 0.01% w/v to 0.03% w/v propylparaben.

Antioxidants

The liquid formulations of the present disclosure may include one or more antioxidants, including, but not limited to, Vitamin E, Vitamin C, butylated hydroxyanisole (BHA), butylated hydroxytoluene (BHT), sodium metabisulfite, potassium metabisulfite, sodium thiosulfate pentahydrate, and the like. The one or more antioxidants may reduce impurities of the liquid formulations.

The one or more antioxidants may be present in an amount of 0.01% w/v to 5.0% w/v. The one or more antioxidants may be present in an amount of at least 0.01% w/v, including, but not limited to, 0.02% w/v, 0.05% w/v, 0.10% w/v, 0.15% w/v, 0.20% w/v, 0.25% w/v, 0.5% w/v, 1.0% w/v, 1.5% w/v, 2.0% w/v, 2.5% w/v, 3.0% w/v, 3.5% w/v, 4.0% w/v, 4.5% w/v, and at least 5.0% w/v. The one or more antioxidants may be present in an amount not more than 5.0% w/v, including, but not limited to, not more than 4.5% w/v, 4.0% w/v, 3.5% w/v, 3.0% w/v, 2.5% w/v, 2.0% w/v, 1.5% w/v, 1.0% w/v, 0.50% w/v, 0.25% w/v, 0.20% w/v, 0.15% w/v, 0.10% w/v, 0.05% w/v, 0.02% w/v, and not more than 0.01% w/v. Any combination of upper and lower limits are possible and within the scope of the present disclosure, including, but not limited to, 0.01% w/v to 0.02% w/v, 0.1% w/v to 0.3% w/v, 0.01% w/v to 0.25% w/v, 0.05% w/v to 0.15% w/v, 0.10% w/v to 0.20% w/v, 0.15% w/v to 0.25% w/v, 0.20% w/v to 0.25% w/v, 0.05% w/v to 0.15% w/v, 0.01% w/v to 5.0% w/v, 0.05% w/v to 5.0% w/v, 0.05% w/v to 0.25% w/v, and 0.25% w/v to 0.50% w/v.

In an exemplary formulation, the antioxidant comprises sodium thiosulfate pentahydrate, included in the liquid formulations at 0.05% w/v to 0.25% w/v.

Viscosity Agents

The rate of drug delivery is influenced by the viscosity. As a non-limiting example, increasing viscosity may slow down rates of drug diffusion. The liquid formulations of the present disclosure may include one or more viscosity agents or thickening agents to increase the viscosity of the liquid formulations. Viscosity agents may include, but are not limited to, plant extracts (e.g., starches, pectin, alginates, carrageenan, acacia gum, tragacanth, cellulose, and the like), seed polysaccharides (e.g., guar gum, locust bean gum, and the like), modified polysaccharides (e.g., modified starches, amidated pectin, propylene glycol alginate, and the like), products of fermentation (e.g., xanthan gum, gellan gum, pullulan, dextran, and the like), cellulose ethers (e.g., microcrystalline cellulose, carboxymethyl cellulose, and the like), animal extracts (e.g., gelatin, chitosan, caseinates, and the like), semi-synthetic hydrocolloids (e.g., methylcellulose, ethylcellulose, hydroxyethylcellulose, hydroxypropylcellulose, Hypromellose, and the like), hydrocolloids, vinyl polymers, water soluble polyvinylpyrrolidones (e.g., povidone and copovidone of molecular weights ranging from 2500 to 1250000 g/mol), ethylene-vinyl acetates, polyvinyl alcohol, aluminum silicates, carbomers (e.g., Carbopol® 910, Carbopol® 940, Carbopol® 941, Carbopol® 934, Carbopol® 934P, 900 series carbomers, (e.g., 934P, 940GE, 974P, 971P, and the like), 1300 series carbomers, and the like), sorbitol, liquid maltitol, sucrose, fructose, dextrose, maltodextrin, polydextrose, natural gum, sodium carboxymethyl cellulose, polyethylene glycol, polyethylene oxide, silica, silicones, glycerin, fatty acids, and saturated fats.

The one or more viscosity agents may be present in an amount of 0.05% w/v to 10% w/v. The one or more viscosity agents may be present in an amount of at least 0.05% w/v, including, but not limited to, 0.05% w/v, 0.25% w/v, 0.50% w/v, 0.75% w/v, 1.0% w/v, 1.25% w/v, 1.50% w/v, 2.0% w/v, 3.0% w/v, 4.0% w/v, 5.0% w/v, 6.0% w/v, 7.0% w/v, 8.0% w/v, 9.0% w/v, and at least 10.0% w/v. The one or more viscosity agents may be present in an amount not more than 10% w/v, including, but not limited to, not more than 10.0% w/v, 9.0% w/v, 8.0% w/v, 7.0% w/v, 6.0% w/v, 5.0% w/v, 4.0% w/v, 3.0% w/v, 2.0% w/v, 1.50% w/v, 1.25% w/v, 1.0, 0.75% w/v, 0.50% w/v, 0.25% w/v, and not more than 0.05% w/v. Any combination of upper and lower limits are possible and within the scope of the present disclosure, including, but not limited to, 0.05% w/v to 0.25% w/v, 0.25% w/v to 0.50% w/v, 0.50% w/v to 0.75% w/v, 0.75% w/v to 1.0% w/v, 1.0% w/v to 1.25% w/v, 1.0% w/v to 2.0% w/v, 2.0% w/v to 5.0% w/v, and 5.0% w/v to 10.0% w/v.

In an exemplary formulation, the viscosity agent comprises carboxymethyl cellulose included in the liquid formulations at 0.1% w/v to 2.5% w/v, such as 0.8% w/v to 1.2% w/v.

Chelating Agents

The liquid formulations of the present disclosure may include one or more chelating agents. Chelating agents are chemical compounds that react with metal ions to form a stable, water-soluble complex. Chelating agents chemically bind and render inactive trace metals that would otherwise have an adverse impact on color, flavor, clarity, and shelf life of liquid formulations. A chelating agent may include, but is not limited to, gluconic acid and salts, citrates and salts, diethylene triamine penta acetic acid (DTPA), phosphate and salts, hydroxycarboxylic acids (e.g., malic acid, tartaric acid, and the like), partially neutralized salts of ethylenediaminetetraacetic acid (EDTA), EDTA, polydentate ligands (e.g., polynucleic acids, polypeptides, proteins, polysaccharides, amino acids, and the like), branded proprietary chelating agents, and the like.

The one or more chelating agents may be present in an amount of 0.01% w/v to 0.5% w/v. The one or more chelating agents may be present in an amount of at least 0.01% w/v, including, but not limited to, at least 0.01% w/v, 0.025% w/v, 0.05% w/v, 0.075% w/v, 0.10% w/v, 0.2% w/v, 0.3% w/v, 0.4% w/v, and at least 0.5% w/v. The one or more chelating agents may be present in an amount not more than 0.5% w/v, including, but not limited to, not more than 0.5% w/v, 0.4% w/v, 0.3% w/v, 0.2% w/v, 0.1% w/v, 0.075% w/v, 0.05% w/v, 0.025% w/v, and not more than 0.01% w/v. Any combination of upper and lower limits are possible and within the scope of the present disclosure, including, but not limited to, 0.01% w/v to 0.025% w/v, 0.025% w/v to 0.050% w/v, 0.050% w/v to 0.10% w/v, 0.10% w/v to 0.20% w/v, 0.20% w/v to 0.30% w/v, 0.30% w/v to 0.40% w/v, and 0.40% w/v to 0.50% w/v.

In an exemplary formulation, the chelating agent comprises edetate disodium (EDTA) included in the liquid formulations at 0.01% w/v to 0.5% w/v, such as 0.02% w/v to 0.25% w/v or 0.025% w/v to 0.0.75% w/v.

Liquid Formulations

An exemplary liquid formulation of the present disclosure includes 1% w/v to 20% w/v of two or more of the sweeteners; 0.1% w/v to 0.75% w/v of two or more of the flavoring agents; 0.3% w/v to 1.0% w/v cevimeline hydrochloride; 60% w/v to 90% w/v of the solvents; and 0.05% w/v to 5.0% w/v of the antioxidant.

Another exemplary liquid formulation of the present disclosure includes 1% w/v to 16% w/v of two or more of the sweeteners; 0.1% w/v to 0.75% w/v of two or more of the flavoring agents; 0.3% w/v to 1.0% w/v cevimeline hydrochloride; 60% w/v to 90% w/v of the solvents; 0.05% w/v to 0.15% w/v of the antioxidant; 0.1% w/v to 0.30% w/v of the preservative; 0.50% w/v to 0.85% w/v of a buffering agent; 0.5% w/v to 1.5% w/v of a viscosity agent; and 0.025% w/v to 0.075% w/v of a chelating agent.

Another exemplary liquid formulation of the present disclosure includes 50% w/v to 70% w/v primary solvent, such as water; 15% w/v to 35% w/v of a cosolvent, such as glycerin and propylene glycol; 0.50% w/v to 0.85% w/v of the buffering agent(s); 0.11% w/v to 0.33% w/v of the preservative(s); 0.5% w/v to 1.50% w/v of the viscosity agent; 0.01% w/v to 0.2% w/v of the chelating agent; 0.05% w/v to 0.25% w/v of the antioxidant; 5.0% w/v to 17.0% w/v of the sweetener(s); 0.06% w/v to 0.30% w/v of the flavoring agent(s); 0.3% w/v to 1.0% w/v cevimeline hydrochloride, and wherein additional primary solvent may be added quantum satis to achieve the desired formulation, i.e., desired final volume or dosage.

Another exemplary liquid formulation of the present disclosure includes 5% w/v to 17% w/v of a sweetener comprising 0.5% w/v to 2.0% w/v of sucralose and 5% w/v to 15% w/v of a 70% solution of sorbitol; a flavoring agent comprising 0.05% w/v to 0.25% w/v of a fruit flavoring agent and 0.01% w/v to 0.05% w/v maltol; 0.6% w/v of cevimeline hydrochloride; 60% w/v to 90% w/v of a solvent; 0.1% w/v to 0.30% w/v of a preservative comprising methyl paraben and propyl paraben; 0.05% w/v to 0.15% w/v sodium thiosulfate pentahydrate; 0.50% w/v to 0.85% w/v of a buffering agent; 0.5% w/v to 1.5% w/v of a viscosity agent; and 0.025% w/v to 0.075% w/v of a chelating agent, wherein the liquid formulation has a pH of 4.0 to 5.7 and comprises less than 0.5% w/v impurities after storage for at least three months at 25° C. and 60% relative humidity or 30° C. and 65% relative humidity.

In another exemplary formulation of the present disclosure, the liquid cevimeline formulation includes those ingredients listed in Table 1.

The liquid formulations of the present disclosure may block or alter taste receptors on the tongue to mask the bitter taste. Components of the liquid formulations may bind to or encapsulate the cevimeline to mask the bitter taste. Unlike the prior art, the liquid formulations of the present disclosure may not result in a decrease in the effectiveness of the one or more active components, including, but not limited to, cevimeline.

The liquid formulations of the present disclosure may be stable at room temperature (20-25° C.) and do not require refrigeration. According to certain aspects, the liquid formulations may be stable at 15° C.-30° C. Stability at room temperature and the lack of refrigeration is advantageous over prior art liquid formulations, as it provides ease of use for patients and increases availability across different temperature ranges. For example, the liquid formulations may comprise less than 0.5% w/v impurities after storage for at least three months at 25° C. and 60% relative humidity, or after storage for at least three months at 30° C. and 65% relative humidity, or after storage for at least two months at 40° C. and 75% relative humidity.

TABLE 1

Liquid Formulation of Cevimeline

| Liquid Formulation | Function | % w/v |
|---|---|---|
| Cevimeline Hydrochloride, USP | Active Pharmaceutical Ingredient | 0.1-1.0 |
| Propylene Glycol, USP | Solubilizer | 5-15 |
| Methyl paraben, NF | Preservative | 0.1-0.3 |
| Propyl paraben, NF | Preservative | 0.01-0.03 |
| Carboxymethylcellulose Sodium, USP | Viscosity Builder | 0.5-1.5 |
| Sorbitol Solution 70%, USP | Sweetener | 5-15 |
| Sucralose, NF | Sweetener | 0.5-1.5 |
| Sodium Citrate Dihydrate, USP | Buffering Agent | 0.30-0.55 |
| Anhydrous Citric Acid, USP | Buffering Agent | 0.2-0.30 |
| Versene NA (Edetate Disodium, USP) | Chelating Agent | 0.01-0.20 |
| Sodium Thiosulfate Pentahydrate, USP | Antioxidant | 0.05-0.25 |
| Glycerin, USP | Cosolvent | 10-20 |
| Artificial Raspberry flavor #998 | Flavoring Agent | 0.05-0.25 |
| Maltol | Flavoring Agent | 0.01-0.05 |
| Purified water, USP | Vehicle | Q.S. 50-70 |

The liquid formulations described herein may be used to treat diseases, as well as conditions, symptoms or adverse effects attributed to such diseases. The liquid formulations may be utilized to treat any disease, condition, symptom, or adverse effects associated with xerostomia or dry mouth.

Accordingly, the present disclosure provides methods of orally administering a cevimeline liquid formulation to or by a patient. The liquid formulations of the present disclosure may be administered at least once a day, including, but not limited to, 1, 2, 3, 4, 5, 6, 7, 8, 9, and 10 administrations per day. Preferably, the liquid formulations of cevimeline may be administered to or by the patient one or two or three times per day, such as two or three times per day.

It should be understood that the specific aspects described herein are only used for explaining the present disclosure rather than limiting it. In addition, it is anticipated that alternative aspects and implementations may be made into sustained-release formulations, suspensions, and/or other ingestible products.

The present disclosure also provides kits that can be used to practice the present disclosure. A kit may comprise at least one component of any liquid formulation described herein, or a liquid formulation described herein. In some aspects, a kit includes liquid formulations, or any of the variations described herein, with a container such as a cup wherein a patient may easily orally administer the liquid formulation. In some aspects, the liquid formulation is included in unit dose or at least one pre-filled syringe. The liquid formulation may be included in a multi-dose container to simplify health and therapeutic regimen for end users.

The shelf-life at room temperature of the liquid formulations of the present disclosure may be at least 6 months, including, without limitation, 6 to 9 months, to 6 to 12 months, 6 to 15 months, 6 to 18 months, 6 to 21 months, 6 to 24 months, 6 to 27 months, 6 to 30 months, 6 to 33 months, and 6 to 36 months. In one aspect, the shelf-life at room temperature is at least 24 months.

The liquid compositions of the present disclosure are "substantially free", "essentially free" or "completely free" of impurities. As used herein, "substantially free" or "essentially free" refers to the presence in trace amounts or less. "Trace amounts" are those quantitative levels of a constituent that are barely detectable and provide no benefit to the functional properties of the subject formulations or efficacy of the formulations in the disclosed methods of use or treatment. For example, a trace amount may constitute 1.0 wt. %, 0.5 wt. %, 0.1 wt. %, 0.05 wt. %, or even 0.01 wt. % of a component of any of the liquid cevimeline formulations disclosed herein. "Totally free", as used herein, is understood to mean completely free of a constituent.

The liquid composition may be used in treatment or alleviation of Sjogren's syndrome, A mammal, such as a human being, may receive the liquid formulation according to the present disclosure 1 to 10 times a day or as needed.

The liquid composition may be used in treatment or alleviation of xerostomia. A mammal, such as a human being, may receive the liquid formulation according to the present disclosure 1 to 10 times a day or as needed.

The liquid composition may be used in treatment or alleviation of dry mouth. A mammal, such as a human being, may receive the liquid formulation according to the present disclosure 1 to 10 times a day or as needed.

In an exemplary method of treating dry mouth or xerostomia, any of the liquid formulations disclosed herein may be administered one, two, or three times per day, such as in a 5 ml dose comprising 30 mg cevimeline hydrochloride.

In an exemplary method of treating Sjögren's syndrome in a patient, any of the liquid formulations disclosed herein may be administered one, two, or three times per day, such as in a 5 ml dose comprising 30 mg cevimeline hydrochloride.

Any methods disclosed herein may comprise one or more steps or actions for performing the described method. The method steps and/or actions may be interchanged with one another. In other words, unless a specific order of steps or actions is required for proper operation of the aspect, the order and/or use of specific steps and/or actions may be modified.

Features are sometimes grouped together in a single aspect or description thereof for the purpose of streamlining the disclosure. This method of disclosure, however, is not to be interpreted as reflecting an intention that any claim require more features than those expressly recited in that claim. Rather, inventive aspects lie in a combination of fewer than all features of any single foregoing disclosed aspect. It will be apparent to those having skill in the art that changes may be made to the details of the above-described aspects without departing from the underlying principles set forth herein.

Likewise, benefits, other advantages, and solutions to problems have been described above with regard to various aspects. However, benefits, advantages, solutions to problems, and any element(s) that may cause any benefit, advantage, or solution to occur or become more pronounced are not to be construed as a critical, a required, or an essential feature or element.

Aspects of the Invention Provided in the Present Disclosure

The present disclosure provides a stable liquid formulation configured for oral administration. The formulation comprises at least one sweetener, at least one flavoring agent, cevimeline hydrochloride, a solvent, and an antioxidant. Any of the below listed ingredients may be included in any combination in the disclosed liquid formulations.

The at least one sweetener may comprise two or more sweeteners selected from the group consisting of: xylitol, sucralose, and sorbitol. The at least one sweetener may comprise sucralose and sorbitol. For example, the sweetener may comprise 1% w/v to 22% w/v of the sweetener, such as about 0.5% w/v to 20% w/v of a solution of sorbitol (e.g., 70% solution) and about 0.5% w/v to 2.0% w/v sucralose.

The flavoring agent may comprise a taste masking agent and/or a natural or artificial fruit flavor. The taste masking agent may comprise maltol. The flavoring agent may comprise a natural or artificial flavoring agent and a taste masking agent such as maltol. For example, the flavoring agent may comprise 0.05% w/v to 0.25% w/v of a flavoring agent and 0.01% w/v to 0.03% w/v maltol.

According to certain aspects, the liquid formulation may comprise two or more sweeteners and two or more flavoring agents configured as a taste masking composition. The taste masking composition may comprise two or more sweeteners selected from the group consisting of: xylitol, sucralose, and sorbitol; and a natural or artificial flavoring agent and maltol. For example, the taste masking composition comprises sucralose, sorbitol, a fruit flavoring agent, and maltol. As a further example, the taste masking composition may comprise about 0.5% w/v to 20% w/v of a solution of sorbitol (e.g., 70% solution), about 0.5% w/v to 2.0% w/v sucralose, about 0.05% w/v to 0.25% w/v of a flavoring agent, and about 0.01 to 0.02% w/v maltol.

The solvent may be included at 60% w/v to 90% w/v. As example, the solvent may comprise one or more solvents selected from water, glycerol, and propylene glycol. In an exemplary formulation, the solvent may comprise 10% w/v to 20% w/v glycerin, 5% w/v to 15% w/v propylene glycol, and water added quantum satis to achieve the desired formulation.

The antioxidant may comprise sodium thiosulfate pentahydrate.

According to certain aspects, the liquid formulation may comprise one or more preservatives. The preservatives may comprise methyl paraben and propyl paraben.

According to certain aspects, the liquid formulation may comprise a chelating agent. The chelating agent may comprise edetate disodium.

According to certain aspects, the liquid formulation may comprise a viscosity builder. The viscosity builder may comprise carboxymethylcellulose Sodium.

According to certain aspects, the liquid formulation may comprise one or more buffers, wherein the liquid formulation has a pH of 3.0 to 7, such as 4.0 to 6.5, or 3.8 to 6, or 4.0 to 5.7, or 4.2 to 5.6, or 4.4 to 5.4, or 4.6 to 5.1, or 4.4 to 4.8.

The liquid formulations provided herein may comprise less than 0.5% w/v impurities after storage for at least three months at 25° C. and 60% relative humidity, or at least three months 30° C. and 65% relative humidity, or at least two months at 40° C. and 75% relative humidity.

According to certain aspects, the liquid formulations provided herein may comprise: 5% w/v to 16% w/v of the sweetener; 0.05% w/v to 0.75% w/v of the flavoring agent, such as 0.1% w/v to 0.2% w/v; 0.3% w/v to 1.0% w/v of the cevimeline hydrochloride; 60% w/v to 90% w/v of the solvent; 0.1% w/v to 0.30% w/v of the preservative; and 0.05% w/v to 0.15% w/v of the antioxidant.

According to certain aspects, the liquid formulations provided herein may further comprise a buffering agent; a viscosity agent; and a chelating agent. An exemplary formulation may comprise 0.50% w/v to 0.85% w/v of a buffering agent; 0.5% w/v to 1.5% w/v of a viscosity agent; and 0.025% w/v to 0.075% w/v of a chelating agent.

The present disclosure provides methods for treating xerostomia comprising administering a liquid formulation one, two, or three times per day, wherein the liquid formulation comprises any of the formulations disclosed herein. In certain aspects, the liquid formulation is administered as a 5 ml dose comprising 30 mg cevimeline.

The present disclosure provides methods for treating Sjögren's syndrome in a patient comprising administering a liquid formulation one, two, or three times per day, wherein the liquid formulation comprises any of the formulations disclosed herein. In certain aspects, the liquid formulation is administered as a 5 ml dose comprising 30 mg cevimeline.

While particular aspects have been illustrated and described, it would be obvious to those skilled in the art that various other changes and modifications may be made without departing from the spirit and scope of the present disclosure. Those skilled in the art will recognize or be able to ascertain using no more than routine experimentation, numerous equivalents to the specific apparatuses and methods described herein, including alternatives, variants, additions, deletions, modifications and substitutions. This application including the appended aspects is therefore intended to cover all such changes and modifications that are within the scope of this application.

EXAMPLES

Example 1: Stability Testing

A liquid formulation according to the present disclosure was tested for stability. The formulation included 0.60% w/v cevimeline hydrochloride and ingredients as disclosed in Table 1. The formulation was tested within three timeframes: post-manufacturing (initial), day 14 of being subjected to 55° C., and 1, 2, and/or 3 months after accelerated conditions (accelerated temperature/condition 40° C.+/−2° C. and 75%+/−5% relative humidity), intermediate conditions (30° C.+/−2° C. and 65%+/−5% relative humidity) or standard conditions (25° C.+/−2° C. and 60%+/−5% relative humidity). The results are shown in Table 2.

TABLE 2

Stability Testing

| | Liquid Cevimeline Formulation | | | | | | | |
|---|---|---|---|---|---|---|---|---|
| | | 55° C. | 40° C., 75% RH | | | 25° C., 60% RH | | 30° C., 65% RH |
| Test | Initial† | 14 Days | 1 Month | 2 Months | 3 Months | 2 Months | 3 Months | 3 Months |
| Description | Clear colorless liquid | NP | Clear colorless liquid | Clear colorless liquid | Clear colorless liquid | Clear colorless liquid | Clear colorless liquid | Clear colorless liquid |
| pH | 4.75 | 4.84 | 4.84 | 4.80 | 4.90 | 4.77 | 4.91 | 4.87 |
| Density ($g/cm^3$) | 1.08 | 1.08 | 1.08 | 1.08 | 1.08 | 1.08 | 1.08 | 1.08 |
| Viscosity (mPa · s) | 90.80 | NP | 85.28 | 94.56 | 86.40 | 91.84 | 89.20 | 86.64 |
| Cevimeline Assay (w/v) | 100.7% | NP | 100.8% | 100.3% | 99.9% | 97.8% | 100.6% | 100.6% |
| EDTA Assay (w/v) | 99.8% | NP | 98.8% | 98.9% | 98.7% | 100.3% | 99.6% | 98.1% |
| Sodium Thiosulfate Pentahydrate Assay (w/v) | 97.3% | NP | 91.8% | 85.7% | 79.6% | 97.5% | 96.0% | 92.8% |
| Methyl paraben (w/v) | 99.7% | NP | 99.6% | 99.8% | 99.4% | 100.2% | 97.2% | 98.3% |
| Propyl paraben (w/v) | 98.6% | NP | 98.3% | 101.4% | 98.9% | 101.7% | 96.7% | 97.7% |
| 3,4-Dihydroxy benzoic Acid (w/v) | ND | NP | ND | ND | ND | ND | ND | ND |
| 4-Hydroxy Benzoic Acid (w/v) | ND | NP | ND | 0.1 | 0.1 | ND | ND | ND |
| 2,4-Dihydroxy benzoic Acid (w/v) | ND | NP | ND | ND | ND | ND | ND | ND |
| Benzoic Acid (w/v) | ND | NP | ND | ND | ND | ND | ND | ND |
| Trans Isomer (w/v) | 0.430% | 0.419% | 0.448% | 0.448% | 0.476% | 0.450% | 0.474% | 0.469% |
| Cis-Sulfoxide Impurity (w/v) | ND | ND | ND | ND | ND | ND | ND | ND |

TABLE 2-continued

Stability Testing

| Test | Liquid Cevimeline Formulation | | | | | | | |
|---|---|---|---|---|---|---|---|---|
| | 55° C. | | 40° C., 75% RH | | | 25° C., 60% RH | | 30° C., 65% RH |
| | Initial† | 14 Days | 1 Month | 2 Months | 3 Months | 2 Months | 3 Months | 3 Months |
| Trans-Sulfoxide Impurity (w/v) | ND | ND | ND | ND | ND | ND | ND | ND |
| QHT (w/v) | ND | ND | ND | ND | ND | ND | ND | ND |
| QTA (w/v) | ND | ND | ND | ND | ND | ND | ND | ND |
| Largest Unspecified Degradation Product (w/v) | ND | ND | ND | ND | 0.063% | ND | ND | ND |
| Total Degradation Products (w/v) | 0.430% | 0.419% | 0.448% | 0.448% | 0.539% | 0.450% | 0.474% | 0.469% |

†Initial expected value or percent of specified amount added;

ND = Not Detected; NP = Not Performed; NMT = Not More Than; RH = relative humidity; QHT is: (3-(mercaptomethyl) quinuclidin-3 ol/3-mercaptomethyl-3-quinuclidinol; QTA is: 1,1-bis[3-hydroxy-3-quinuclidinyl methylthio] ethane/3,3'-((Ethane-1,1-diylbis(sulfanedyl))bis(methylene))bis(quinuclidine-3-ol).

Example 2: Selection of an Antioxidant

While cevimeline hydrochloride is soluble in aqueous formulations, it is not recommended to store such formulations for more than a day and to protect the formulations from heat. However, as demonstrated by the data in Table 1, the presently disclosed formulations are in fact very stable for long periods at elevated temperatures. The present inventors have developed the cevimeline formulations to include a specific mixture and amount of certain antioxidants, chelating agents, buffers, and preservatives that significantly stabilize the formulations.

A variety of antioxidants are known to be useful as preservatives during storage of pharmaceuticals, including sulfur-containing antioxidants, free thiols, such as cysteine, homocysteine, thioglycerol, acetylcysteine, as well as sodium sulfite, sodium metabisulfite, sodium thiosulfate, and the like, disulfides (such as dithiothreitol and α-lipoic acid where free thiols can be generated), and other classes of antioxidants, such as ascorbic acid, gallic acid and its derivatives, tocopherol and its derivatives, and others known in the art to prevent oxidation. However, selection of an antioxidant that will work for a particular active pharmaceutical ingredient is often not predictable. For example, the well-known antioxidant benzalkonium chloride has been found to have no significant impact on cevimeline stability when included in an aqueous solution configured for ophthalmic or intranasal administration.

TABLE 3

Impact of Sodium Thiosulfate Pentahydrate

| Test/Condition | Specifications | Formulation A (Batch with Sodium Thiosulfate Pentahydrate) | | Formulation B (Batch without Sodium Thiosulfate Pentahydrate) | |
|---|---|---|---|---|---|
| | | Initial | Day 14@ 55° C. | Initial | Day 14@ 55° C. |
| pH | 4.6-5.1 | 4.75 | NP | 4.77 | NF |
| Density (g/mL) | 097-1.18 | 1.075 | NF | 1.078 | NP |
| Cevimeline Assay (w/v) | 90.0% to 110.0% | 98.3% | 98.3% | 97.4% | 97.9% |
| Trans Isomer (w/v) | NMT 1.2% | 0.299% | 0.282% | 0.290% | 0.301% |
| Cis-Sulfoxide Impurity (w/v) | NMT 0.22% | 0.028% | 0.040% | ND | 0.318% |
| Trans-Sulfoxide Impurity (w/v) | NMT 0.22% | ND | 0.066% | 0.032% | 0.362% |
| QHT (w/V) | NMT 0.22% | ND | ND | 0.008% | ND |
| QTA (w/V) | NMT 0.22% | 0.030% | 0.055% | 0.252% | 0.550% |
| Largest Unknown (w/v) | NMT 0.20% | ND | ND | ND | ND |
| Total impurities (w/v) | NMT 2.0% | 0.357% | 0.443% | 0.582% | 1.531% |

ND = Not Detected;

NP = Not Performed;

NMT = Not More Than;

QHT is: (3-(mercaptomethyl) quinuclidin-3 ol/3-mercaptomethyl-3-quinuclidinol;

QTA is: 1,1-bis[3-hydroxy-3-quinuclidinyl methylthio] ethane/3,3'-((Ethane-1,1-diylbis(sulfanedyl))bis(methylene) bis(quinuclidine-3-ol).

The present inventors have tested various antioxidants and found that sodium thiosulfate pentahydrate was the most effective antioxidant, even when included at very low concentrations. For example, an exemplary liquid formulation of the present disclosure includes sodium thiosulfate pentahydrate at a concentration as low as 0.1% w/v, which was found to effectively reduce or essentially eliminate formation of degradation products of the disclosed compositions, even when stored at higher temperatures (e.g., 55° C.; see Table 3). Certain other antioxidants, such as ascorbic acid, were found to be incompatible with the liquid formulations of the present disclosure and failed to provide sufficient protection against the formation of degradation products.

As shown in Table 3, the stability of a liquid formulation of the present disclosure was tested with and without sodium thiosulfate pentahydrate as a preservative and anti-oxidating agent (see Table 1). The formulation with 0.1% w/v sodium thiosulfate pentahydrate (Formulation A) remained stable even after 14 days at 55° C. while the formulation absent sodium thiosulfate pentahydrate (Formulation B) demonstrated a significant increase in impurities, exceeding specification limits at the same testing parameters. In additional testing, not shown, various other concentrations of sodium thiosulfate pentahydrate were tested. Unexpectedly, higher concentrations (e.g., 2.2% w/v) of the sodium thiosulfate pentahydrate, while effective as an antioxidant, were found to produce a cloudy or hazy solution.

Example 3: pH Stability Testing pH stability testing was performed on two cevimeline liquid formulations of the present disclosure. Formulation C was adjusted to a pH of 4.0 using 0.1 N hydrochloric acid. Formulation D was adjusted to a pH of 6.5 using 0.1 N sodium hydroxide. The liquid formulations included 0.60% w/v cevimeline hydrochloride, purified water as a primary solvent, two cosolvents, three preservatives, a viscosity agent, two sweeteners, two buffering agents, a chelating agent, artificial raspberry flavoring agent, and an artificial flavoring agent (taste masking agent; see Table 1).

The stability of liquid formulations C and D was tested within three timeframes: post-manufacturing (initial), day 15 of being subjected to 55° C. and 1M of being Accelerated (40° C.). The stability results shown in Table 4 indicate that formulations of the present disclosure remain stable in the pH range 4.0 to 6.5 at 55° C. for up to 14 days and at 40° C. for up to 1M (see Table 4). The results also demonstrate that the lower pH sample, i.e., formulation C, may be as stable as, or even slightly more stable than, the pH 6.5 sample, i.e., formulation D, as demonstrated by the total impurities noted after long term storage at elevated temperatures (1 month at 40° C., 75% RH). This is unexpected as prior work with an aqueous formulation of cevimeline demonstrated that formulations having a pH of 7.0 to 7.4 were more stable when stored at elevated temperatures (i.e., 6 months at 60° C.) than formulations having a pH of 6.0 (see WO 2023/147318 at Table 6). The present inventors have thus developed aqueous formulations of cevimeline having a pH within the range of 4.2 to 5.6, such as 4.4 to 5.4, or 4.6 to 5.1, or even 4.4 to 4.8.

TABLE 4 pH stability testing

| Test/Condition | Specifications | Formulation C Initial | Formulation C Day 15@ 55° C. | Formulation C 1M@ 40° C., 75% RH | Formulation D Initial | Formulation D Day 15@ 55° C. | Formulation D 1M@ 40° C., 75% RH |
|---|---|---|---|---|---|---|---|
| pH | 4.0-6.5 | 3.98 | 4.10 | 4.13 | 6.45 | 6.43 | 6.51 |
| Density (g/mL) | 097-1.18 | 1.069 | 1.071 | 1.066 | 1.078 | 1.074 | 1.074 |
| Viscosity (cP) | 70-110 | 51.52 | NP | 53.44 | 93.84 | NP | 95.12 |
| Cevimeline Assay (w/v) | 90.0% to 110.0% | 91.4 | NP | NP | 101.5 | NP | NP |
| Trans Isomer (w/v) | NMT 1.2% | 0.376 | 0.384 | 0.421 | 0.370 | 0.333 | 0.412 |
| Cis-Sulfoxide Impurity (w/v) | NMT 0.22% | ND | ND | ND | ND | ND | ND |
| Trans-Sulfoxide Impurity (w/v) | NMT 0.22% | ND | ND | ND | ND | ND | ND |
| QHT (w/v) | NMT 0.22% | ND | ND | ND | ND | ND | ND |
| QTA (w/v) | NMT 0.22% | ND | ND | ND | ND | ND | ND |
| Largest Unknown (w/v) | NMT 0.20% | ND | 0.044 | ND | ND | ND | 0.031 |
| Total impurities (w/v) | NMT 2.0% | 0.376 | 0.428 | 0.421 | 0.370 | 0.333 | 0.443 |

ND = Not Detected; NP = Not Performed; NMT = Not More Than; RH = relative humidity; QHT is: (3-(mercaptomethyl) quinuclidin-3 ol/3-mercaptomethyl-3-quinuclidinol; QTA is: 1,1-bis[3-hydroxy-3-quinuclidinyl methylthio] ethane/3,3'-((Ethane-1,1 diylbis(sulfanedyl))bis(methylene))bis(quinuclidine-3-ol).

Example 4: Selection of a Viscosity Building Agent

Various viscosity building agents were also tested in the liquid formulations of the present disclosure. The liquid formulations included 0.60% w/v cevimeline hydrochloride, purified water as a primary solvent, two cosolvents, three preservatives, two sweeteners, two buffering agents, a chelating agent, and artificial raspberry flavoring agent, wherein Formulation E included 0.35% w/v hydroxyethyl cellulose (HEC) and Formulation F included 1.0% w/v carboxymethyl cellulose (CMC). The stability of liquid formulations E and F was tested within three timeframes: post-manufacturing (initial) and days 4 and 14 of being subjected to 55° C. The results are noted in Table 5.

TABLE 5

| Stability Testing of Viscosity Building Agents | | | | | | | |
|---|---|---|---|---|---|---|---|
| | | Formulation E | | | Formulation F | | |
| Test/Condition | Specifications | Initial | Day 4@ 55° C. | Day 14@ 55° C. | Initial | Day 4@ 55° C. | Day 14@ 55° C. |
| Trans Isomer (w/v) | NMT 1.2% | 0.238 | 0.241% | 0.185% | 0.191% | 0.195% | 0.152% |
| Trans Sulfoxide Impurity (w/v) | NMT 0.22% | ND | ND | ND | ND | ND | ND |
| QHT (w/v) | NMT 0.22% | ND | ND | ND | ND | ND | ND |
| Largest Unspecified Degradation product (w/v) | NMT 0.20% | 0.018% | 0.023% | 0.225% | ND% | 0.024% | 0.077% |
| Total Degradation product (w/v) | NMT 2.0% | 0.257% | 0.264% | 0.597% | 0.191% | 0.219% | 0.246% |

NMT = Not More Than; ND = Not Detected; QHT is: (3-(mercaptomethyl) quinuclidin-3 ol/3-mercaptomethyl-3-quinuclidinol; pH of the test formulation was 4.6-4.8.

While both viscosity building agents demonstrated acceptable increases in viscosity (0.35% w/v HEC viscosity 215.2 mPa s, 1.0% w/v CMC viscosity 139.5 mPa s), Formulation F comprising the CMC demonstrated better stability and "mouth feel" than Formulation E comprising the HEC.

Example 5: Selection of a Sweetener

Various sweeteners were tested in the liquid formulations of the present disclosure. The liquid formulations included 0.60% w/v cevimeline hydrochloride, purified water as a primary solvent, two cosolvents, two preservatives, two buffering agents, a chelating agent, and various sweeteners: Formulation G—20% w/v xylitol, Formulation H—10% w/v or 70% solution of sorbitol, Formulation I—0.1% w/v aspartame, and Formulation J—0.5% w/v sodium saccharin. The stability of liquid formulations G-J was tested within three timeframes: post-manufacturing (initial) and days 4 and 14 of being subjected to 55° C. The results are noted in Table 6.

TABLE 6

| Stability Testing of Sweeteners | | | | | |
|---|---|---|---|---|---|
| | Number days at 55° C. | Trans Isomer (% w/v) | Sulfoxide Impurity (% w/v) | Largest Unspecified Degradation product (% w/v) | Total Degradation product (% w/v) |
| Formulation G-Xylitol | Initial | 0.305 | ND | ND | 0.305% |
| | 4 | 0.311 | 0.067 | 0.074 | 0.510 |
| | 14 | 0.338 | 0.110 | 0.145 | 0.772 |
| Formulation H-Sorbitol | Initial | 0.303 | ND | ND | 0.303 |
| | 4 | 0.309 | 0.065 | 0.076 | 0.450 |
| | 14 | 0.339 | 0.078 | 0.144 | 0.717 |
| Formulation I-Aspartame | Initial | 0.315 | 0.043 | ND | 0.358 |
| | 4 | 0.629 | 0.067 | 0.109 | 1.008 |
| | 14 | 0.664 | 0.115 | 0.146 | 1.350 |
| Formulation J-Sodium Saccharin | Initial | 0.338 | ND | ND | 0.338 |
| | 4 | 0.316 | ND | 0.151 | 0.552 |
| | 14 | 0.372 | 0.072 | 0.363 | 1.119 |

Stability testing of the formulations comprising Aspartame and Sodium Saccharin (formulations I and J, respectively) demonstrated higher levels of degradation products at day 14 of storage than the formulations comprising xylitol and sorbitol (formulations G and H, respectively).

Example 6: Taste Studies of 6 mg/mL Cevimeline Liquid Formulation

An Alpha-MOS e-tongue was used for taste masking evaluation of a 6 mg/mL cevimeline hydrochloride liquid formulation of the present disclosure (0.60% w/v cevimeline hydrochloride). The bitterness masking effect was estimated by the determination of the distances from the e-tongue signal of the formulation with cevimeline and the formulation without cevimeline (placebo).

Testing was performed using the Astree e-tongue system (SN: AST-5052; Alpha MOS, Toulouse, France) equipped with an Alpha MOS sensor set #6 composed of 7 sensors (AHS (Serial No. 79207-12002534-102B), PKS (Serial No. 79601-11003595-105D), CTS (Serial No. 78914-11003448-104A), NMS (Serial No. 79317-11003522-105A), CPS (Serial No. 79007-11003347-104B), ANS (Serial No. 78912-11003429-104A), and SCS (Serial No. 79204-12003016-102B)) on a 48 position autosampler using 25 mL beakers. The AHS, CTS, and NMS are sourness, saltiness, and umami sensors respectively, while PKS, CPS, ANS, and SCS are general-purpose sensors. These sensors are modified solid electrochemical electrodes based on well-established technology: Chemical Sensitive Field Effect Transistor (ChemFETs).

All data generated on the Astree system was evaluated using multidimensional statistics on AlphaSoft V2023 software. Prior to analysis of the formulation, the sensors were conditioned in 0.01 M hydrochloric acid for six hours and calibrated in 0.01 M hydrochloric acid for one hour. A diagnostic was completed in in 0.01 M hydrochloric acid, 0.01 M sodium chloride, and 0.01 M monosodium glutamate solutions to evaluate performance of the sensors.

The sample volume was 25 mL with a 120 second acquisition time and 300 seconds time per analysis. The e-tongue signal in each solution was measured at equilibrium on seven (7) sensors (average between 100 and 120 seconds). Three replicates were taken, and the sensors were cleaned with milli Q water (ultrapure water) between each measurement from one sample to another to avoid cross-contamination.

Taste comparison with the Alpha MOS e-tongue was based on comparison of overall taste profiles of analyzed samples. The e-tongue signals were processed via Principal Component Analysis (PCA). The PCA computed a set of axes that capture the maximum variance in the data set. The x-axis (PC1) represents the dominant variance that demonstrates the significance in discrimination. The y-axis (PC2)

is orthogonal and explains residual variation. The PCA taste map enables the estimation of distance between the centers of gravity for the clusters of data samples. The distance, the Euclidean distance (ED), is the distance between the centers of the cluster of one sample set to the center of the cluster of another sample set. Them middle of the cluster generated from three data points per sample represents the center of gravity. The ED is used to assess the similarity or difference between each pair of samples. The lower the distance, the closer the taste.

FIG. 1 represents the overall taste comparison between purified water (WO), purified water+cevimeline hydrochloride (C51), placebo for cevimeline hydrochloride oral solution 6 mg/mL (C49), and cevimeline liquid formulations (6 mg/mL) of the present disclosure (C47, C61) with the most discriminative of the seven sensors (CPS, NMS). The placebo (C49) included purified water, preservatives, a viscosity agent, a sweetener, Cavasol® W7 HP Pharma, a solvent, a cosolvent, a buffering agent, and two flavoring agents. The cevimeline liquid formulations (C47, C61) included purified water, cevimeline hydrochloride, preservatives, a viscosity agent, a sweetener, a chelating agent, an antioxidant, a solvent, a cosolvent, a buffering agent, and two flavoring agents, one of which was maltol (see Table 1).

The distance between C49 and C61 is [C49-C61], which was found to be 176 (FIG. 1)—the shortest distance of all the pairs analyzed. This is interpreted as enough taste masking effect on bitterness in the formulation C61, i.e., the active formulation C61 comprising cevimeline and the placebo formulation C49 absent cevimeline were similar in taste.

Example 7: Human Tongue Testing

The described formulations were also evaluated using a human tongue testing procedure. Each of the inventive and comparative formulations were manufactured to include 60% w/v to 70% w/v primary solvent (water); 15% w/v to 35% w/v of a cosolvent (glycerin and propylene glycol); 0.50% w/v to 0.85% w/v of the buffering agent(s); 0.11% w/v to 0.33% w/v of the preservative(s); 5% w/v to 15% w/v of a 70% solution of sorbitol; 0.5% w/v to 1.5% w/v viscosity builder (carboxymethylcellulose sodium); and 0.6% w/v cevimeline. The remaining ingredients are listed in Table 7. In addition, several taste controls for salty, sweet, and sour flavors were included, as well as a placebo formulation comprising the formulation ingredients absent cevimeline, and a cevimeline control comprising 0.6% w/v cevimeline in water.

TABLE 7

Inventive and Comparative Formulations

| | Inventive | | | | Comparative | | | |
|---|---|---|---|---|---|---|---|---|
| Ingredients (% w/v) | A | B | C | D | A | B | C | D |
| Cyclodextrin | — | — | — | — | 10.00 | — | — | — |
| EDTA | 0.05 | 0.05 | 0.05 | 0.05 | — | 0.05 | 0.05 | 0.05 |
| Sodium Thiosulfate Pentahydrate | 0.10 | 0.10 | 0.10 | 0.10 | — | 0.10 | 0.10 | 0.10 |
| Artificial flavor | 0.10 | 0.10 | 0.10 | — | 0.10 | — | — | — |
| Maltol A | 0.50 | | 0.50 | 0.50 | — | | — | — |
| Natural flavor masker | 10.00 | — | — | | 10.00 | — | 0.50 | — |
| Natural Modulation Flavor masking (IFF) | — | — | — | — | — | — | — | 0.50 |
| Maltol B | — | 0.015 | — | — | — | — | — | — |
| Sucralose, NF | 1.00 | 1.00 | 1.00 | 1.00 | 1.00 | 1.00 | 1.00 | 1.00 |

Maltol A—solution of <3% maltol in >90% propylene glycol. Maltol B—100% powdered maltol. Artificial flavor is an artificial raspberry flavor. Natural flavor masker is a mixture of propylene glycol, glycerine, monoammoniated glycyrrhizin, and natural flavor.

Purified water (WO) is discriminated from C51. This indicates that the e-tongue was sensitive to cevimeline hydrochloride. WO, C51, C49, and C61 were the most discriminated samples. C61 was the closest to placebo (C49) and the most distant to C51 (see FIG. 1). Sample C61 includes the taste masking composition: maltol, sorbitol, sucralose, and a fruit flavoring agent).

Taste Comparison

The Euclidian distances between the formulations were calculated to assess taste proximity between samples: the lower the distance, the closer the taste. A discrimination index (DI in %) was determined for each sample. This indicator takes into account the average difference between the pairs to compare, as well as the dispersion of each sample. The closer the index to 100%, the greater the distance between the centers of gravity and the smaller the dispersion within groups. Thus, the DI will help to assess the significance of differences between the groups. DI >90% suggest a significant taste difference.

The repeatability of the measurements was determined for each sample on three replicates, and the standard deviations were within acceptable ranges (SD<100).

A 5 mL sample from each formulation was placed into glass test tubes and appropriately labeled. Using a pipette, a few drops of each sample were directly administered into the mouth. The sample was swirled in the mouth and then spat out. The study was conducted as a blinded test, where participant/subject was unaware of the sample identities or their contents. Additionally, to ensure the accuracy of the taste assessment, participant was intermittently given control samples: a citric acid solution (to assess sour taste), a sucralose solution (to assess sweet taste), and a sodium chloride solution (to assess salty taste). These control samples confirmed that participants' taste perception was reliable, and that the testing integrity was maintained (see Table 8).

Observation for Human Tongue Testing

The data provided in Table 8 demonstrates that compositions (Inventive A-D) formulated with a taste masking composition of the present disclosure (i.e., two or more sweeteners and two or more a flavoring agents) provide excellent palatability, demonstrating good sweetness, i.e., Inventive A-D all rated good to excellent in taste, and little to no bitter or sour taste.

On the other hand, formulations absent the taste masking composition of the present disclosure were generally not very palatable. Comparative formulation A, manufactured with cyclodextrin, was bitter (3) despite moderate sweetness (3). Cyclodextrin is a macrocyclic oligosaccharide that can form cavities that act as molecular containers with the ability to trap guest molecules therein. The resulting inclusion complexes have been used in taste masking applications for other pharmaceutical formulations. The results in Table 8 demonstrate that while cyclodextrin may be effective to mask flavors of other pharmaceuticals, it was not effective at masking the bitter taste of cevimeline. Similar results were observed in an e-tongue assay (not shown).

Comparative formulation B, which included two sweeteners but lacked any artificial or natural flavors or commercial flavor masking agents exhibited bitterness (3) and minimal sweetness (1), indicating the flavoring agents and/or taste masking agents have an important role in masking the bitter taste of the cevimeline in the liquid formulations.

Other formulations, such as comparative C and D, which included two sweeteners and a natural flavor or taste masking agent also suffered from noticeable bitterness and aftertaste issues, while the control (0.6% w/v cevimeline in water) was the least favorable due to its extremely high bitterness (5) with no sweetness or sourness. Controls like citric acid and sucralose solutions highlighted the challenges of balancing sweetness and sourness while avoiding bitter aftertastes.

A clear comparison between the various samples highlights the superior performance of the inventive formulations A-D. Inventive formulations A, C, and D, manufactured with a maltol solution (solution of <3% maltol in >90% propylene glycol) demonstrated low bitterness (1), moderate sweetness (3), and no sourness, resulting in a well-balanced taste profile rated as "Good." Similarly, Inventive formulation B, manufactured using a powdered maltol, exhibited no bitterness, high sweetness (4), and no sourness, earning it the highest rating as "Excellent in taste."

In aggregate, these results demonstrate that the inventive compositions comprising cevimeline and a taste masking composition that includes two or more sweeteners, a flavoring agent, and a taste masking agent such as maltol, provide excellent palatability. Moreover, a comparison of the taste profile of Inventive C and D demonstrates that while inclusion of a flavoring agent improves the taste profile, a good taste profile may also be achieved absent the flavoring agent, as long as maltol is included; see Comparative A, which includes a flavoring agent but is absent maltol and has a very poor taste profile (bitterness of 3).

TABLE 8

Human Taste Testing Results

| Batch/Details | Rating: 0 (LOW) to 5 (HIGH) bitter | Sweet | Sour | Mouth feel/ Taste masking |
|---|---|---|---|---|
| Salt Water (1% w/v NaCl in $H_2O$) | 0 | 0 | 0 | Salty |
| Citric Acid Soln (1% w/v in $H_2O$) | 0 | 0 | 5 | Sour |
| Sucralose Soln (5% w/v in $H_2O$) | 1 | 4 | 0 | Sweet, but bitter aftertaste |
| Mixture of Salt + Sucralose and Citric acid | 1 | 4 | 4 | Sweet, Sour and Salty |
| Control A – Inventive A w/o cevimeline | 0 | 3 | 0 | Good |
| Control B – cevimeline in water | 5 | 0 | 0 | Bitteres† among all |
| Inventive-A | 1 | 3 | 0 | Good |
| Inventive-B | 0 | 4 | 0 | Excellent in taste |
| Inventive-C | 2 | 1 | 1 | Good |
| Inventive-D | 1 | 2 | 0 | Good |
| Comparative A | 3 | 3 | 1 | Bittert in taste |
| Comparative B | 3 | 2 | 1 | Bitter in taste |
| Comparative C | 1 | 2 | 1 | Bitter Aftertaste |
| Comparative D | 1 | 2 | 2 | Bitter Aftertaste |

†0.5% w/v caffeine in $H_2O$ used as a standard for bitterness.

Surprisingly, the results in Table 8 demonstrate that only maltol effectively masked the bitter taste of the active pharmaceutical ingredient (API), whereas other commonly used taste-masking agents failed to produce comparable results. For example, Comparative D included a natural modulation flavor masker (sold by International Flavors & Fragrances), yet was found to be sour and to have a bitter aftertaste. Comparison of Inventive A, which includes maltol and a second commercially available flavor masking agent, and Comparative A, which is absent maltol but includes the same commercially available flavor masking agent, demonstrates that only maltol is able to mask the bitter taste of the cevimeline. As such, the unique efficacy of maltol in providing taste masking suggests a specific and previously unrecognized interaction with cevimeline.

CONCLUSION

Based on the results of stability testing, human taste testing, and electronic tongue (e-tongue) testing, the present inventors have found the presently disclosed compositions, which comprise a unique combination of pH-modifying agents, antioxidant, and a specialized taste masking composition, demonstrate excellent stability and palatability. Moreover, the results provided herein demonstrate that this novel combination of pH-modifying agents, antioxidant, and a specialized taste masking composition function collectively to enhance both the stability and palatability of a formulation containing cevimeline.

What is claimed is:

1. A liquid formulation for oral administration comprising:

0.60% w/v cevimeline hydrochloride;

1% w/v to 16% w/v of a taste masking composition comprising two or more sweeteners and two or more flavoring agents, wherein one of the two or more flavoring agents comprises maltol;

60% w/v to 80% w/v of a solvent;

0.1% w/v to 0.30% w/v of a preservative; and 0.05% w/v to 5.00% w/v of an antioxidant, wherein the liquid formulation has a pH of 4.0 to 5.7 and comprises less than 0.5% w/v impurities after storage for at least three months at 25° C. and 60% relative humidity or 30° C. and 65% relative humidity.

2. The liquid formulation of claim 1, wherein the taste masking composition comprises:

two or more sweeteners selected from the group consisting of: xylitol, sucralose, and sorbitol; and a natural or artificial flavoring agent and the maltol.

3. The liquid formulation of claim 1, wherein the taste masking composition comprises sucralose, sorbitol, a flavoring agent, and the maltol.

4. The liquid formulation of claim 3, comprising about 1% w/v sucralose, about 10% w/v of a 70% solution of sorbitol, and 0.01 to 0.02% w/v maltol.

5. The liquid formulation of claim 1, wherein the solvent comprises water and glycerin.

6. The liquid formulation of claim 1, wherein the solvent comprises water, glycerin, and propylene glycol.

7. The liquid formulation of claim 1, wherein the preservative comprises methyl paraben and propyl paraben.

8. The liquid formulation of claim 1, wherein the antioxidant comprises sodium thiosulfate pentahydrate.

9. The liquid formulation of claim 1, further comprising:

0.50% w/v to 0.85% w/v of a buffering agent;

0.5% w/v to 1.5% w/v of a viscosity agent; and 0.025% w/v to 0.075% w/v of a chelating agent.

10. The liquid formulation of claim 9, wherein the viscosity agent comprises carboxymethylcellulose sodium.

11. The liquid formulation of claim 9, wherein the chelating agent comprises edetate disodium.

12. A liquid formulation for oral administration comprising:

1% w/v to 16% w/v of a sweetener;

0.1% w/v to 0.75% w/v of a flavoring agent comprising maltol;

0.3% w/v to 1.0% w/v of cevimeline hydrochloride;

60% w/v to 80% w/v of a solvent;

0.1% w/v to 0.30% w/v of a preservative; and 0.05% w/v to 0.15% w/v of an antioxidant;

0.50% w/v to 0.85% w/v of a buffering agent;

0.5% w/v to 1.5% w/v of a viscosity agent; and 0.025% w/v to 0.075% w/v of a chelating agent, wherein the liquid formulation has a pH of 4.0 to 5.7 and comprises less than 0.5% w/v impurities after storage for at least three months at 25° C. and 60% relative humidity or 30° C. and 65% relative humidity.

13. The liquid formulation of claim 12, wherein the sweetener comprises sorbitol and sucralose, the flavoring agent comprises a natural or artificial fruit flavoring agent and the maltol, and the antioxidant comprises sodium thiosulfate pentahydrate.

14. The liquid formulation of claim 13, comprising about 1% w/v sucralose, about 10% w/v of a 70% solution of sorbitol, and 0.01 to 0.02% w/v maltol.

15. The liquid formulation of claim 12, wherein the solvent comprises water, glycerin, and propylene glycol.

16. The liquid formulation of claim 12, wherein the preservative comprises methyl paraben and propyl paraben.

17. The liquid formulation of claim 12, wherein the antioxidant comprises sodium thiosulfate pentahydrate.

18. A liquid formulation configured for oral administration comprising:

a sweetener comprising about 1% w/v sucralose and about 10% w/v of a 70% solution of sorbitol;

a flavoring agent comprising 0.05% w/v to 0.25% w/v of a fruit flavoring agent and 0.01% w/v to 0.03% w/v maltol;

0.6% w/v of cevimeline hydrochloride;

60% w/v to 80% w/v of a solvent;

0.1% w/v to 0.30% w/v of a preservative comprising methyl paraben and propyl paraben;

0.05% w/v to 0.15% w/v sodium thiosulfate pentahydrate;

0.50% w/v to 0.85% w/v of a buffering agent;

0.5% w/v to 1.5% w/v of a viscosity agent; and 0.025% w/v to 0.075% w/v of a chelating agent, wherein the liquid formulation has a pH of 4.0 to 5.7 and comprises less than 0.5% w/v impurities after storage for at least three months at 25° C. and 60% relative humidity or 30° C. and 65% relative humidity.

19. A method of treating xerostomia comprising:

administering a 5 ml dose of a liquid formulation one, two, or three times per day, wherein the liquid formulation comprises the liquid formulation according to claim 1, and wherein the 5 ml dose comprises 30 mg cevimeline hydrochloride.

20. A method of treating Sjögren's syndrome in a patient, the method comprising:

administering a 5 ml dose of a liquid formulation one, two, or three times per day, wherein the liquid formulation comprises the liquid formulation according to claim 1, and wherein the 5 ml dose comprises 30 mg cevimeline hydrochloride.

21. A liquid formulation for oral administration comprising:

0.60% w/v cevimeline hydrochloride;

1% w/v to 16% w/v of a taste masking composition comprising one or more sweeteners and one or more flavoring agents, wherein the one or more flavoring agents comprise maltol;

60% w/v to 80% w/v of a solvent;

0.1% w/v to 0.30% w/v of a preservative; and 0.05% w/v to 5.00% w/v of an antioxidant, wherein the liquid formulation has a pH of 4.0 to 5.7 and comprises less than 0.5% w/v impurities after storage for at least three months at 25° C. and 60% relative humidity or 30° C. and 65% relative humidity.

* * * * *